(12) United States Patent
Tao et al.

(10) Patent No.: US 9,354,237 B2
(45) Date of Patent: May 31, 2016

(54) METHODS FOR ISOLATING PROTEINS

(71) Applicant: Purdue Research Foundation, West Lafayette, IN (US)

(72) Inventors: Weiguo Andy Tao, West Lafayette, IN (US); Li Yang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 98 days.

(21) Appl. No.: 14/387,082

(22) PCT Filed: Mar. 13, 2013

(86) PCT No.: PCT/US2013/030841
§ 371 (c)(1),
(2) Date: Sep. 22, 2014

(87) PCT Pub. No.: WO2013/172942
PCT Pub. Date: Nov. 21, 2013

(65) Prior Publication Data
US 2015/0080248 A1 Mar. 19, 2015

Related U.S. Application Data

(60) Provisional application No. 61/649,059, filed on May 18, 2012.

(51) Int. Cl.
*G01N 1/34* (2006.01)
*G01N 33/68* (2006.01)
*C07K 1/22* (2006.01)

(52) U.S. Cl.
CPC .............. *G01N 33/6848* (2013.01); *C07K 1/22* (2013.01); *G01N 1/34* (2013.01); *G01N 2458/00* (2013.01); *G01N 2560/00* (2013.01)

(58) Field of Classification Search
None
See application file for complete search history.

(56) References Cited

U.S. PATENT DOCUMENTS

| 4,739,044 | A  | 4/1988  | Stabinsky |
| 4,757,141 | A  | 7/1988  | Fung et al. |
| 7,825,227 | B2 | 11/2010 | Boniface et al. |
| 8,163,305 | B2 | 4/2012  | Bednarski et al. |
| 8,361,485 | B2 | 1/2013  | Naughton et al. |

OTHER PUBLICATIONS

Methods of Cell and Tissue: Laboratory Procedures, John Wiley & Sons Ltd., Chichester, England 1996, Freshney (1987).
Culture of Animal Cells: A Manual of Basic Technique, 2nd Ed., A.R. Liss. Inc., New York, Ch. 20. pp. 257-288 (1987).
Kambara et al., Bio/Technol., 6:816-21, 1998.
Smith et al.,"The synthesis of oligonucleotides containing an aliphatic amino group at the 5' terminus: synthesis of fluorescent DNA primers for use in DNA sequence analysis" Nucl. Acid Res., 13:2399-2412, 1985.
Smith, et al., "Fluorescence detection in automated DNA sequence analysis," Nature, 321: 674-679, 1986.
Oligonucleotides and Analogues: A Practical Approach, IRL Press, Oxford, 1991.
Zuckerman et al., "Efficient methods for attachment of thiol specific probes to the Y-ends of synthetic oligodeoxyribonucleotides" Polynucleotides Res. 15: 5305-5321, 1987.
Sharma et al.,"A general method for the synthesis of 3'-sulfhydryl and phosphate group containing oligonucleotides" Polynucleotides Res., 19: 3019, 1991.
Giusti et al., "Synthesis and Characterization of f'-Fluorescent-dye-labeled Oligonucleotides" PCR Methods and Applications, 2: 223-227, 1993.
Agrawal et al., "Site-Specific Functionalization of Oligodeoxynucleotides for Non-Radioactive Labelling" Tetrahedron Letters, 31: 1543-1546, 1990.
Sproat et al., "The synthesis of prtected 5'-mercapto-2',5'-dideoxyribonucleoside-3'-O-phosphoramidites; uses of 5'-mercapto-oLigodeoxyribonucleotides" Polynucleotides res., 15: 4837, 1987.
Nelson et al.,"Bifunctional oligonucleotide probes synthesized using a novel CPG support are able to detect single base pair mutations." Polynucleotides Res. 17: 7187-7194. 1989.
Gundry et al., "Preparation of proteins and peptides for mass spectrometry analysis in a bottom-up proteomics workflow" Curr. Protoc. Mol. Biol. 2009: Chapter 10.
Zlatic S.A., Ryder P.V., Salazar G., Faundez V. (2010). Isolation of Labile Multi-protein Complexes by in vivo Controlled Cellular Cross-Linking and Immuno-magnetic Affinity Chromatography. JoVE. 37. http://www.jove.com/index/Details.stp?ID=1855, doi: 10.3791/1855.
Brandenburg B, Lee LY, Lakadamyali M, Rust MJ, Zhuang X, et al. (2007) Imaging poliovirus entry in live cells. PLoS Biol 5(7): e183. doi:10.1371/journal.pbio.0050183.
Ewers et al. "Analysis of Virus Entry and Cellular Membrane Dynamics by Single Particle Tracking," Methods in Enzymology, vol. 506 (2012) pp. 63-80.
Hsu T-H, Spindler KR (2012) Identifying Host Factors That Regulate Viral Infection. PLoS Pathog 8(7): e1002772. doi:10.1371/journal.ppat.1002772.
Puig, et al. "The Tandem Affinity Purification (TAP) Methods: A General Procedure of Protein Complex Purification", Methods 24, 218-229 (2001).
van der Schaar HM, Rust MJ, Chen C, van der Ende-Metselaar H, Wilschut J, et al. (2008) Dissecting the Cell Entry Pathway of Dengue Virus by Single-Particle Tracking in Living Cells. PLoS Pathog 4(12): e1000244. doi:10.1371/journal.ppat.1000244.
ThermoScientific "Crosslinking Protein Interaction Analysis", http://www.piercenet.com/browse, 2013.

*Primary Examiner* — Jacob Cheu
(74) *Attorney, Agent, or Firm* — Brown Rudnick LLP; Adam M. Schoen

(57) ABSTRACT

The invention generally relates to methods for isolating proteins. In certain aspects, methods of the invention involve preparing a plurality of sample preparations, each preparation including one or more intact cells. A capture unit is introduced to a plurality of the preparations. The capture unit includes a member that transiently interacts with one or more proteins in the cells and a reactive functional group. The sample preparations are incubated, and a reaction is initiated at a different time in a plurality of the preparation. In this manner, a protein within the cell that specifically interacts with the member of the capture unit becomes bound to the capture unit via the reactive functional group to form protein/capture unit complexes. The cells are lysed and the protein/capture unit complexes are isolated.

22 Claims, 17 Drawing Sheets

Clathrin-mediated (CME)

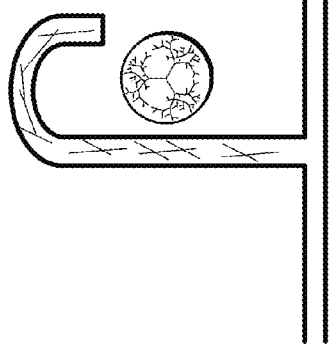

Macropinocytosis

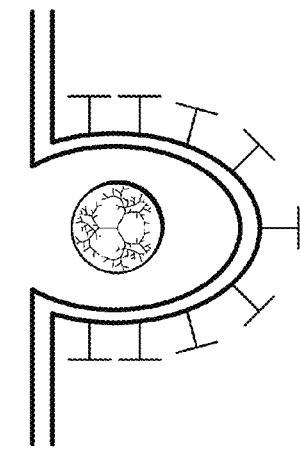

| Functions | Cellular factors (CME) | Cellular Factors (Macropinocytosis) |
|---|---|---|
| Coat protein | Clathrin heavychain | None |
| Adaptors | AP2 (AP2B1) *espin 1* | Unknown |
| Scission Factors | *Dynamin-2* | None |
| Regulatory Factors | Cortactin (CTTN), Arp2/3 (ARPC5) | PAK1, PKC (kinases), Ras, Rac1 (GTPase), Na⁺/H⁺ exchangers |
| Cytoskeleton | Actin, microtubules | Anti, microtubules (actin dependent) |
| Trafficking | Rab 7 (RAB7A), Rab11 (RAB11A) | Rab7, Arf6 (Arf3, Arf4) |

\* Unique ID in Bold; ID not identified in *italic*.

FIG. 12A

METHODS FOR ISOLATING PROTEINS

RELATED APPLICATION

The present application is a 35 U.S.C. §371 national phase patent application of PCT/US13/30841, filed Mar. 13, 2013, which claims the benefit of and priority to U.S. provisional application Ser. No. 61/649,059, filed May 18, 2012, the content of each of which is incorporated by reference herein in its entirety.

GOVERNMENT SUPPORT

This invention was made with government support under RR025802 awarded by National Institutes of Health. The government has certain rights in the invention.

FIELD OF THE INVENTION

The invention generally relates to methods for isolating proteins.

BACKGROUND

In living cells, complex processes are typically accomplished by highly specific binding interactions among functional cell components, most commonly involving one or more proteins. Understanding which proteins bind to one another, and under what circumstances, poses difficult unsolved problems. An approach to learning which proteins bind to each other to form protein complexes is to isolate functional protein complexes, or portions thereof, in order to identify their components.

However, the dynamic nature of cellular machineries is frequently built on transient and/or weak protein associations. Those low affinity interactions preclude stringent methods for the isolation and identification of protein networks around a protein of interest. In fact, most in vivo protein-protein binding is transient and occurs only briefly to facilitate signaling or metabolic function. Capturing or freezing those momentary contacts to study which proteins are involved and how they interact is difficult.

For example, following single virus particles during an initial phase of infection, that is, virus entry into target cells, can reveal crucial information on the mechanism of pathogen infections and likewise cellular transport and membrane dynamics. A problem with studying viral entrance pathways is that virus entry is highly dynamic. The subsequent interactions of the virus with cellular structures during the various entry steps (binding, plasma membrane dynamics, internalization/endocytosis, intracellular trafficking, penetration/membrane fusion) are transient, and they require motion of the virion. Additionally, the virus interacts with cellular structures that are dynamic themselves.

An approach that has been used to study viral entry is to optically label virus particles and then follow the particles in real time as they infect a cell. However, several challenges are associated with the analysis of viral entry in live cells using optically labeled viral particles. Practical challenges lie within the detection noise of the sample, that is, how reliably viral particles or cellular structures can be discerned from background noise. Additionally, in the infective processes, particularly quick, transient events, are not synchronized. Different virions within a population may follow different itineraries at the time of acquisition. Alternatively, a single virus may exhibit several different types of motion during the time of data acquisition such as diffusion, directed motion, confinement (on the plasma membrane) followed by fast long range intracellular movement. In addition, the ratios of overall virus particles to infectious particles can be high, and this may make it difficult to define the relevant motion patterns of infectious particles as opposed to the biological noise of noninfectious particles.

SUMMARY

The invention provides methods for analyzing cellular entrance pathways and isolating proteins for analysis along those pathways. Methods of the invention can be used to analyze any molecular interactions, such as protein-protein interactions, and are particularly useful for analyzing cellular machinery that interacts with viruses as they enter and infect cells. Of particular importance, methods of the invention provide a time lapse analysis, providing an ability to capture and isolate different proteins along different places of an entrance pathway. In this manner, methods of the invention allow for many different proteins along a cellular entry pathway to be captured and isolated. Additionally, methods of the invention are accomplished without the need for optical labels, and therefore are able to overcome the problems associated with analyzing entrance pathway using labeled entities, such as labeled virus particles.

Aspects of the invention are accomplished by preparing a plurality of sample preparations, each preparation including one or more intact cells. A capture unit is introduced to each of the preparations. The capture unit includes a member that transiently interacts with one or more proteins in the cells and a reactive functional group. The sample preparations are incubated, and a reaction is initiated at a different time a plurality of the preparations. In this manner, a protein within the cell that specifically interacts with the member of the capture unit becomes bound to the capture unit via the reactive functional group to form protein/capture unit complexes. The cells are lysed and the protein/capture unit complexes isolated. In essences, methods of the invention provide the means for capturing molecular interactions, such as protein-protein complexes or virus/protein complexes, by binding them together as they interact. The rapid reactivity allows even transient interactions to be frozen in place or weakly interacting molecules to be seized in a complex stable enough for isolation and characterization. By initiating the reactions at different times, different proteins along an entry pathway are captured in the different preparations. Accordingly, the isolated proteins represent the numerous proteins found along a single entry pathway.

The number of sample preparations will depend on the number of analysis time points desired. The invention is not limited to any specific number of preparations, for example, there can be two, three, four, five, ten, 15, 20, 40, 100, etc. preparations. The reaction in each preparation is initiated at a different time. No specific time points are required, and one of skill in the art can determine the time points that they wish to use for initiating the reactions. In an exemplary embodiment, the method uses three sample preparations, in which the reaction is initiated in a first sample preparation after 30 minutes of incubation, the reaction is initiated in a second sample preparation after 60 minutes of incubation, and the reaction is initiated in a third sample preparation after 120 minutes of incubation.

Typically, the member is capable of entering the cells through a native entrance pathway of the cell. The reactive functional moiety does not interfere with the specific interaction between the member and the proteins within the cell. As mentioned above, methods of the invention may be used to study any type of molecular interactions. Accordingly, the interaction to be studied will determine the type of member used in the capture unit. For example, the member may be a protein, a drug, a nucleic acid, a protein, a nanoparticle, a dendrimer, an antibody, or a microorganism. Exemplary microorganisms are viruses, bacteria, and fungi. However, the invention is not limited to any specific type of member.

Numerous different reactive moieties may be used with methods of the invention. In certain embodiments, the reactive functional group is a crosslinking reagent. The crosslinking reagent is generally designed to bind specific amino acid functional groups on proteins. Exemplary reactive crosslinking moieties include those target amines, sulfhydryls, carboxyls, carbonyls, or hydroxyls. The reactive functional group may be homobifunctional (identical reactive moieties on both ends) or heterobifunctional (different reactive moieties on both ends). The reactive functional group may include a spacer arm between the coupling point to the member and the terminal end. The reactive functional group may be cleavable or noncleavable. The reactive functional group may be water soluble or water insoluble. When using a chemical reactive functional group, typically, a chemical is used to initiate the reaction in each preparation. Exemplary chemicals that may be used to initiate the reaction are formaldehyde, disuccinimidyl suberate (DSS), and Dithiobis[succinimidyl propionate] (DSP).

In other embodiments, the reactive functional group is a photoreactive functional group. Such a reactive functional group remains inert until activated by light, typically UV light. Thus, in these embodiments, light is used to initiate the reaction in each preparation.

It is possible to purify the protein/capture unit complexes from the sample preparations using any protein purification technique known in the art. In certain embodiments, the capture unit further includes a purification handle that facilitates the purification process. For example, the handle can be used in an affinity purification to help separate the protein/capture unit complexes from the sample preparations.

At this point, the proteins may be dissociated from the capture unit. The dissociation may be accomplished by any method that does not affect the isolated protein. The isolated proteins are then analyzed, which may be by any technique known in the art. An exemplary analysis technique uses a mass spectrometer, such as analysis by liquid chromatography-mass spectrometry (LC-MS). Optionally, the capture unit may also include a detectable label, such as an optically detectable label, that may facilitate analysis or any other aspect of the method. The optical label also provides the option of monitoring the capture units in real-time as they proceed through an entry pathway.

There are numerous uses for methods of the invention. For example, methods of the invention may be used to study virus (or other pathogenic particle) cellular entry mechanism for better anti-viral drug design. Methods of the invention may also be used to dissect nano-medicine delivery mechanisms for better efficiency of future nano-medicines.

BRIEF DESCRIPTION OF THE DRAWINGS

FIGS. 12A-B are diagraph identifying endocytic pathways.

DETAILED DESCRIPTION

Figure 1A:
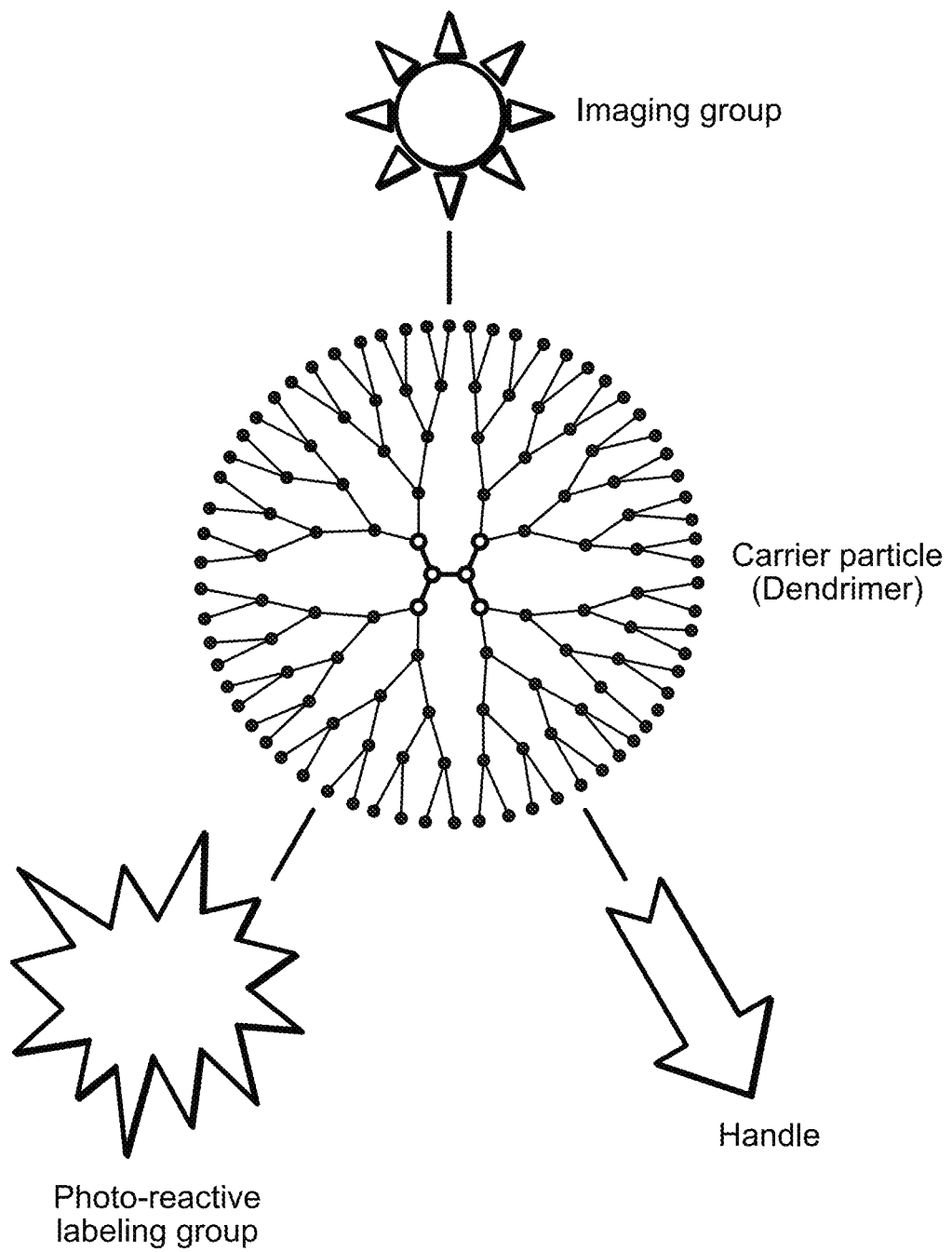
FIG. 1A is a diagram showing the structure of an engineered dendrimer. In general, the engineered dendrimer has a photo-reactive labeling functional group, a handle to enable affinity purification and an imaging group to allow light microscopy and flow cytometry experiments.

The invention generally relates to methods for isolating proteins. In certain aspects, methods of the invention involve preparing a plurality of sample preparations, each preparation including one or more intact cells. A capture unit is introduced to each of the preparations. The capture unit includes a member that transiently interacts with one or more proteins in the cells and a reactive functional group. The sample preparations are incubated, and a reaction is initiated at a different time in each preparation. In this manner, a protein within the cell that specifically interacts with the member of the capture unit becomes bound to the capture unit via the reactive functional group to form protein/capture unit complexes. The cells are lysed and the protein/capture unit complexes are isolated.

The sample may be any material that is to be examined as long as it includes at least one intact cell. The sample may be an environmental sample, a plant sample, or an animal sample, such as a mammalian animal sample. Typically, a sample will be a tissue or body fluid, such as a human tissue or body fluid that is obtained in any clinically acceptable manner. A tissue is a mass of connected cells and/or extracellular matrix material, e.g. skin tissue, endometrial tissue, nasal passage tissue, CNS tissue, neural tissue, eye tissue, liver tissue, kidney tissue, mammary gland tissue, placental tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to, mucous, blood, plasma, serum, serum derivatives, bile, blood, maternal blood, phlegm, saliva, sweat, amniotic fluid, menstrual fluid, mammary fluid, follicular fluid of the ovary, fallopian tube fluid, peritoneal fluid, urine, and cerebrospinal fluid (CSF), such as lumbar or ventricular CSF. The body fluid will generally include intact cells. A sample may also be a fine needle aspirate or biopsied tissue. A sample also may be media containing cells or biological material. A sample may also be a blood clot, for example, a blood clot that has been obtained from whole blood after the serum has been removed.

Methods of the invention then involve preparing a plurality of sample preparations. The number of sample preparations will depend on the number of analysis time points desired. The invention is not limited to any specific number of preparations, for example, there can be two, three, four, five, ten, 15, 20, 40, 100, etc. preparations. Methods of the invention are not limited to any specific technique for preparing the sample preparations. In one embodiment, a plurality of samples from a single source are obtained, and each obtained sample becomes its own sample preparation. In another embodiment, a single sample is obtained and that sample split into a plurality of individual sample preparations. Combinations of those embodiments may also be used to prepare the sample preparations. Regardless of how the sample preparations are obtained, they are maintained under standard cell culture conditions so that the cells and associated proteins remain viable. The cells may be maintained and cultured in any manner known in the art including in monolayer, beads or in three-dimensions and by any means (i.e., culture dish, roller bottle, a continuous flow system, etc.). Methods of cell and tissue culturing are well known in the art, and are described, for example, in Cell & Tissue Culture: Laboratory Procedures, John Wiley & Sons Ltd., Chichester, England 1996; Freshney (1987), Culture of Animal Cells: A Manual of Basic Technique, $2^{nd}$ Ed., A. R. Liss, Inc., New York, Ch. 20, pp. 257-288, (1987), the content of each of which is incorporated by reference herein in its entirety.

Typically, cells are grown and maintained at an appropriate temperature and gas mixture (typically, 37° C., 5% $CO_2$ for mammalian cells) in a cell incubator. Culture conditions vary widely for each cell type, and variation of conditions for a particular cell type can result in different phenotypes. Specifics culture conditions for various cells types are shown for example in Naughton, et al. (U.S. Pat. No. 8,361,485), the content of which is incorporated by reference herein in its entirety.

Aside from temperature and gas mixture, the most commonly varied factor in culture systems is the growth medium. Recipes for growth media can vary in pH, glucose concentration, growth factors, and the presence of other nutrients. The growth factors used to supplement media are often derived from animal blood, such as calf serum. In certain embodiments, chemically defined media is used. Types of growth media, are shown from example in Cell & Tissue Culture Laboratory Procedures, John Wiley & Sons Ltd., Chichester, England 1996; Freshney (1987), Culture of Animal Cells: A Manual of Basic Technique, $2^{nd}$ Ed., A.R. Liss, Inc., New York, Ch. 20, pp. 257-288, (1987); and Naughton, et al. (U.S. Pat. No. 8,361,485).

Plating density (number of cells per volume of culture medium) plays an important role for some cell types. For example, a lower plating density makes granulosa cells exhibit estrogen production, while a higher plating density makes them appear as progesterone-producing theca lutein cells. The skilled artisan will know the proper plating density of the cells being used in a particular assay.

Cells can be grown either in suspension or adherent cultures. Some cells naturally live in suspension, without being attached to a surface, such as cells that exist in the bloodstream. There are also cell lines that have been modified to be able to survive in suspension cultures so they can be grown to a higher density than adherent conditions would allow. Adherent cells require a surface, such as tissue culture plastic or microcarrier, which may be coated with extracellular matrix components to increase adhesion properties and provide other signals needed for growth and differentiation. Most cells derived from solid tissues are adherent. Another type of adherent culture is organotypic culture, which involves growing cells in a three-dimensional (3-D) environment as opposed to two-dimensional culture dishes. This 3D culture system is biochemically and physiologically more similar to in vivo tissue. 3D cell culturing is described, for example in Naughton, et al. (U.S. Pat. No. 8,361,485).

In the case of adherent cultures, the media can be removed directly by aspiration, and then is replaced. Media changes in non-adherent cultures involve centrifuging the culture and re-suspending the cells in fresh media.

In certain embodiments, a sample is prepared as a single culture and passaging is used to produce the plurality of sample preparations, each of which is then separately maintained. Suspension cultures are easily passaged with a small amount of culture containing a few cells diluted in a larger volume of fresh media. For adherent cultures, cells first need to be detached; this is commonly done with a mixture of trypsin-EDTA; however, other enzyme mixes are now available for this purpose. A small number of detached cells can then be used to seed a new culture.

A capture unit is introduced to a plurality of the preparations. The capture unit includes a member that transiently interacts with one or more proteins in the sample preparation, on a surface of the cells, or in the cells. As mentioned above, methods of the invention may be used to study any type of molecular interactions. Accordingly, the interaction or entrance pathway to be studied will determine the type of member used in the capture unit. For example, the member may be a protein, a drug, a nucleic acid, a protein, a nanoparticle, a dendrimer, an antibody, or a microorganism. Exemplary microorganisms are viruses, bacteria, and fungi. However, the invention is not limited to any specific type of member. Typically, the member is capable of entering the cells through a native entrance pathway of the cell.

In certain embodiments, methods of the invention are used to investigate viral entrance pathways. In those embodiments, the member is a virus. Any viruses may be used with methods of the invention. A virus generally refers to a small infectious agent that can replicate only inside the living cells of an organism (plant or animal). Virus particles (known as virions) typically consist of two or three parts: i) the genetic material made from either DNA or RNA; ii) a protein coat that protects those genes; and in some cases iii) an envelope of lipids that surrounds the protein coat when they are outside a cell. The shapes of viruses range from simple helical and icosahedral forms to more complex structures.

The capture unit also includes a reactive functional group. The reactive group provides a mechanism for capturing transient molecular interactions, such as protein-protein or protein-virus interactions. The reactive functional group is configured to react with the proteins that interact with the capture unit, covalently binding the protein to the capture unit as they interact. The rapid reactivity of reactive group allows even transient interactions to be frozen in place or weakly interacting molecules to be seized in a complex stable enough for isolation and characterization.

The reactive functional group may be any structure that is able to react with proteins in the sample preparations. The reactive functional moiety does not interfere with the specific interaction between the member and the proteins in the sample preparation, on the cell surface, or within the cell. Without be limited by any particular theory or mechanism of action, it is believed that only a small number of protein functional groups have selectable targets for practical bioconjugation methods. One selectable target is primary amines ($-NH_2$). This group exists at the N-terminus of each polypeptide chain and in the side chain of lysine (Lys, K) residues. Because of its positive charge at physiologic conditions, primary amines are usually outward-facing (i.e, on the outer surface) of proteins; thus, they are usually accessible for conjugation without denaturing protein structure. Another selectable target is carboxyls ($-COOH$). This group exists at the C-terminus of each polypeptide chain and in the side chains of aspartic acid (Asp, D) and glutamic acid (Glu, E). Like primary amines, carboxyls are usually on the surface of protein structure. Another selectable target is sulfhydryls ($-SH$). This group exists in the side chain of cysteine (Cys, C). Often, as part of a protein's secondary or tertiary structure, cysteines are joined together between their side chains via disulfide bonds ($-S-S-$). In certain embodiments, these disulfide bonds are first reduced to sulfhydryls to make them available for crosslinking by most types of reactive groups. Another selectable target is carbonyls ($-CHO$). These aldehyde groups can be created by oxidizing carbohydrate groups in glycoproteins. For each of these protein functional-group targets, there exist one to several types of reactive groups that are capable of targeting them and are used by methods of the invention as the basis for synthesizing the reactive functional group of the capture unit.

The reactive functional group is selected on the basis of its chemical reactivity (i.e., specificity for particular function groups) and other chemical properties that facilitate its use in different specific applications. In certain embodiments, the reactive functional group carries reactive moieties that target amines, sulfhydryls, carboxyls, carbonyls or hydroxyls. The reactive functional group may be homobifunctional (identical reactive moieties on both ends) or heterobifunctional (different reactive moieties on both ends).

The reactive functional group may include a spacer arm between the coupling point to the member and the terminal end. The spacer allows the reactive group at the terminal end of the reactive functional group to be spatially separated by the spacer from the member, which allows the capture of amino acids that are varying distances apart. In certain embodiments, zero-length reactive functional groups may be used, which bind the capture unit to the protein without leaving any part of the reactive functional group remaining in the interaction after the reaction is completed.

The reactive functional group may be cleavable or non-cleavable. For example, the reactive functional group may be designed to include cleavable elements, such as esters or disulfide bonds, to reverse or break the linkage by the addition of hydroxylamine or reducing agents, respectively. In other embodiments, the reactive functional group may be water soluble or water insoluble. For example, the reactive functional group may be hydrophobic to allow passage into hydrophobic protein domains or through the cell membrane. Alternatively, the reactive functional group may be hydrophilic to limit reactions to aqueous compartments.

Many different reactive functional groups can be synthesized when different combinations of two are more reactive groups are incorporated into capture unit. When combined with different sizes and types of chemical spacer arms, it is possible to generate may different types of the reactive functional groups.

In certain embodiments, the reactive functional group employs carboxyl-to-amine chemistries. EDC and other carbodiimides are zero-length reactive functional group, and they cause direct conjugation of carboxylates ($-COOH$) to primary amines ($-NH_2$) without becoming part of the final interaction (amide bond) between target molecules. EDC crosslinking reactions are generally performed in conditions devoid of extraneous carboxyls and amines. Acidic (pH 4.5 to 5.5) MES buffer (4-morpholino-ethane-sulfonic acid) is most effective, but phosphate buffers at pH≤7.2 are also compatible with the reaction chemistry. N-hydroxysuccinimide (NHS) or its water-soluble analog (Sulfo-NHS) is often included in EDC coupling protocols to improve efficiency or to create a more stable, amine-reactive intermediate.

In certain embodiments, the reactive functional group employs amine-reactive chemistries. NHS esters are reactive groups formed by EDC-activation of carboxylate molecules. NHS ester-activated crosslinkers and labeling compounds react with primary amines in slightly alkaline conditions (pH 7.2-8.5) to yield stable amide bonds. The reaction releases N-hydroxysuccinimide (MW 115), which can be removed easily by dialysis or desalting. NHS— ester crosslinking reactions are usually performed in phosphate buffer at pH 7.2-8.0 for 0.5 to 4 hours at room temperature or 4° C. Primary amine buffers such as Tris (TBS) are not compatible because they compete for reaction; however, in some procedures, it is useful to add Tris or glycine buffer at the end of a conjugation procedure to quench (stop) the reaction. Sulfo-NHS esters are identical to NHS esters except that they contain a sulfonate (—$SO_3$) group on the N-hydroxysuccinimide ring. This charged group has no effect on the reaction chemistry, but it does tend to increase the water-solubility of crosslinkers containing them. In addition, the charged group prevents Sulfo-NHS crosslinkers from permeating cell membranes, enabling them to be used for cell surface crosslinking methods.

Imidoester crosslinkers react with primary amines to form amidine bonds. To ensure specificity for primary amines, imidoester reactions are best done in amine-free, alkaline conditions (pH 10), such as with borate buffer. Because the resulting amidine bond is protonated, the crosslink has a positive charge at physiological pH, much like the primary amine which it replaced. For this reason, imidoester crosslinkers may be used to study protein structure and molecular associations in membranes and to immobilize proteins onto solid-phase supports while preserving the isoelectric point (pI) of the native protein. With imidoesters, the amidine bonds formed are reversible at high pH.

In certain embodiments, the reactive functional group employs sulfhydryl-reactive chemistries. Maleimide-activated crosslinkers and labeling reagents react specifically with sulfhydryl groups (—SH) at near neutral conditions (pH 6.5-7.5) to form stable thioether linkages. Disulfide bonds in protein structures (e.g., between cysteines) should be reduced to free thiols (sulfhydryls) to react with maleimide reagents. Extraneous thiols (most reducing agents) should be excluded from maleimide reaction buffers, because they will compete for coupling sites.

Most haloacetyl crosslinkers contain an iodoacetyl or a bromoacetyl group. Haloacetyls react with sulfhydryl groups at physiologic to alkaline conditions (pH 7.2 to 9), resulting in stable thioether linkages. To limit free iodine generation, which has the potential to react with tyrosine, histidine and tryptophan residues, the iodoacetyl reactions should be performed in the dark.

Pyridyl disulfides react with sulfhydryl groups over a broad pH range to form disulfide bonds. As such, conjugates prepared using these crosslinkers are cleavable with typical disulfide reducing agents, such as dithiothreitol (DTT). During the reaction, a disulfide exchange occurs between the —SH group of the target molecule and the 2-pyridyldithiol group of the crosslinker. Pyridine-2-thione (MW 111; λmax 343 nm) is released as a byproduct that can be monitored spectrophotometrically and removed from protein conjugates by dialysis or desalting.

In certain embodiments, the reactive functional group employs carbonyl-reactive chemistries. Carbonyls (aldehydes and ketones) can be produced in glycoproteins and other polysaccharide-containing molecules by mild oxidation of certain sugar glycols using sodium meta-periodate. Hydrazide-activated crosslinkers and labeling compounds will then conjugate with these carbonyls at pH 5 to 7, resulting in formation of hydrazone bonds. Hydrazide chemistry is useful for labeling, immobilizing or conjugating glycoproteins through glycosylation sites, which are often (as with most polyclonal antibodies) located at domains away from the key binding sites whose function one wishes to preserve. Alkoxyamine compounds conjugate to carbonyls (aldehydes and ketones) in much the same manner as hydrazides.

In certain embodiments, the reactive functional group incorporates photoreactive groups, which react at selected times and only in response to irradiation by light, such as UV light. In certain embodiments, the photoreactive group uses aryl azides (also called phenylazides). When an aryl azide compound is exposed to UV light, it forms a nitrene group that can initiate addition reactions with double bonds or insertion into C—H and N—H sites or can undergo ring expansion to react with a nucleophile (e.g., primary amine). Reactions can be performed in a variety of amine-free buffer conditions to conjugate proteins or even molecules devoid of the usual functional group "handles".

Diazirines are another type of photoreactive group. The diazirine (azipentanoate) moiety has better photostability than phenyl azide groups, and it is more easily and efficiently activated with long-wave UV light (330-370 nm). Photoactivation of diazirine creates reactive carbene intermediates. Such intermediates can form covalent bonds through addition reactions with any amino acid side chain or peptide backbone. Diazirine-analogs of amino acids can be incorporated into protein structures by translation, enabling specific recombinant proteins to be activated as the crosslinker.

In certain embodiments, the capture unit is configured to have a single type of reactive functional group attached. For example, all of the reactive functional groups on a single capture unit are identically configured. In other embodiments, different reactive functional groups are attached to a single capture unit. For example, a single capture unit can include reactive function groups that target primary amines and reactive function groups that target carboxyls. Certain reactive functional groups may have spacers, while others do not. Certain reactive functional groups be water soluble while other are water insoluble. Any combination of any of the above may be placed onto a single capture unit. In still other embodiments, heterogeneity is achieved by mixing differently functionalized capture units. For example, capture units with reactive function groups that target primary amines may be mixed with capture units with reactive function groups that target carboxyls. In another example, capture units with reactive function groups that are water soluble may be mixed with capture units with reactive function groups that are water insoluble. Any combination of differently functionalized captures units may be used with methods of the invention.

The reactive functional group may be attached to the member by any mechanism known in the art. For example, the reactive function groups can be designed to have two active ends. A first reaction can be conducted between the member and the reactive functional group so that one terminal end of the reactive functional group becomes bound to the member, leaving the other terminal end exposed for reaction with proteins in the sample preparations. As discussed above, the reactive functional groups can be designed to have the same terminal ends, so that there is no different between the end that binds the member and the end that binds the free further subsequent reactions. Alternatively, the reactive functional groups can be designed to have different terminal ends, so that the reaction used to bind the reactive functional group to the member is different from the reaction between the free end and the proteins in the sample preparations. When using nanoparticles, the surfaces of those particles can be coated with a reactive moiety that reacts with one end of the reactive functional group. For example, the nanoparticles can be coated with epoxides and the reactive functional group can have an end that is a primary amine that will react with the epoxide and become bound to the nanoparticle. Binding pairs, such as biotin and streptavidin, can be also be used to link reactive functional groups to the member of the capture unit.

The capture units are introduced to a plurality of the sample preparations and the sample preparations are incubated so that the capture unit has time to proceed along its native entrance pathway and into the cells in the sample preparations. A reaction is initiated in a plurality of the preparations. Initiating the reactions causes a protein within the cell that specifically interacts with the member of the capture unit to become bound to the capture unit via the reactive functional group to form protein/capture unit complexes. An important aspect of the invention is that the reaction in initiated at different times in a plurality of the preparations. By initiating the reactions at different times, different proteins along an entry pathway are captured in the different preparations. Accordingly, the isolated proteins represent the numerous proteins found along a single entry pathway. No specific time points are required, and one of skill in the art can determine the time points that they wish to use for initiating the reactions. Any number of time points may be used. For examples, reactions can be initiated less than one minute apart, one minute apart, two minutes apart, five minutes apart, 10 minutes apart, 15 minutes apart, 20 minutes apart, 25 minutes apart, 30 minutes apart, 1 hour apart, etc. The same time interval does not need to be used between each reaction. For example, the first and second reaction may be initiated 30 minutes apart and the second and third reaction may be initiated 60 minutes apart. Additionally, more than one sample preparation may be used for each time point. For example, two samples preparations may be used for each time point, three samples preparations may be used for each time point, four samples preparations may be used for each time point, five samples preparations may be used for each time point, 10 samples preparations may be used for each time point, 20 samples preparations may be used for each time point, etc.

In an exemplary embodiment, the method uses three sample preparations, in which the reaction is initiated in a first sample preparation after 30 minutes of incubation, the reaction is initiated in a second sample preparation after 60 minutes of incubation, and the reaction is initiated in a third sample preparation after 120 minutes of incubation. Such an embodiment is exemplary and not limiting of the invention. By conducting methods in this manner, the first preparation captures proteins that are in contact with the capture unit 30 minutes after the capture units are introduced to the sample preparation. Initiating the reaction freezes the proteins that transiently interact with the capture units at the 30 minute time point along the entrance pathway. Since a reaction has not been initiated in the other preparations, the capture units in those preparations continue along the entrance pathway. The second preparation captures proteins that are in contact with the capture unit 60 minutes after the capture units are introduced to the sample preparation. Initiating the reaction freezes the proteins that transiently interact with the capture units at the 60 minute time point along the entrance pathway. Since a reaction has not been initiated in the other preparations, the capture units in those preparations continue along the entrance pathway. The third preparation captures proteins that are in contact with the capture unit 120 minutes after the capture units are introduced to the sample preparation. Initiating the reaction freezes the proteins that transiently interact with the capture units at the 120 minute time point along the entrance pathway.

Initiation of the reaction will depend on the type of reactive functional group. If the reactivity of the reactive functional group used is triggered by addition of a chemical that reacts with the proteins in the sample preparations and the reactive functional group, then it is the additional that chemical that initiates the reaction. For example, the capture unit can have a reactive functional group that terminates with a primary amine. The primary amine will not react on its own with the proteins in the sample. However, the addition of a chemical, such as formaldehyde, will cause a reaction to occur between the primary amine on the reactive functional group and the formaldehyde. Similarly, the formaldehyde will react with primary amines on the proteins. Thus, the addition of formaldehyde initiates a crosslinking reaction between the capture unit and the proteins that are interacting with the capture unit at that time. Accordingly, it is the addition of the formaldehyde to the sample preparation that initiates the reaction. Other exemplary reactive chemicals include disuccinimidyl suberate (DSS), and Dithiobis[succinimidyl propionate] (DSP).

In an exemplary embodiment, the method uses three sample preparations, in which the reaction is initiated in a first sample preparation after 30 minutes of incubation, the reaction is initiated in a second sample preparation after 60 minutes of incubation, and the reaction is initiated in a third sample preparation after 120 minutes of incubation. The capture unit uses a primary amine as the reactive functional group, and additional of the chemical formaldehyde to initiate the reactions at different time points. Such an embodiment is exemplary and not limiting of the invention. In this embodiment, formaldehyde is added to the first sample preparation 30 minutes after the capture units have been introduced to the preparation. In this manner, the first preparation captures proteins that are in contact with the capture unit 30 minutes after the capture units are introduced to the sample preparation. Initiating the reaction freezes the proteins that transiently interact with the capture units at the 30 minute time point along the entrance pathway. Since formaldehyde has not been added to the other preparations, a reaction has not been initiated in the other preparations, so the capture units in those preparations continue along the entrance pathway. Formaldehyde is then added to the second sample preparation 60 minutes after the capture units have been introduced to the preparation. That initiates the reaction and causes the capture units in the second preparation to capture proteins that are in contact with the capture unit 60 minutes after the capture units are introduced to the sample preparation. Initiating the reaction freezes the proteins that transiently interact with the capture units at the 60 minute time point along the entrance pathway. Since a reaction has not been initiated in the other preparations, the capture units in those preparations continue along the entrance pathway. Formaldehyde is then added to the third sample preparation 120 minutes after the capture units have been introduced to the preparation. That initiates the reaction and causes the capture units in the third preparation to capture proteins that are in contact with the capture units 120 minutes after the capture units are introduced to the sample preparation. Initiating the reaction freezes the proteins that transiently interact with the capture units at the 120 minute time point along the entrance pathway.

If the reactivity of the reactive functional group is photoreactive, then it is the addition of light, such as UV light, that initiates the reaction in each preparation. For example, the capture unit can have a reactive functional group that terminates with an aryl azide or a diazirine. The aryl azide or a diazirine will not react on its own with the proteins in the sample. However, the addition of a light, such as UV light, will cause a reaction to occur between the photoreactive group at the terminal end of the reactive functional group and the proteins. Thus, the addition of light initiates a crosslinking reaction between the capture unit and the proteins that are interacting with the capture unit at that time. Accordingly, it is the addition of the light to the sample preparation that initiates the reaction.

In an exemplary embodiment, the method uses three sample preparations, in which the reaction is initiated in a first sample preparation after 30 minutes of incubation, the reaction is initiated in a second sample preparation after 60 minutes of incubation, and the reaction is initiated in a third sample preparation after 120 minutes of incubation. The capture unit uses a azide or a diazirineas the reactive functional group, and additional of UV light to initiate the reactions at different time points. Such an embodiment is exemplary and not limiting of the invention. In this embodiment, UV light is irradiated onto the first sample preparation 30 minutes after the capture units have been introduced to the preparation. In this manner, the first preparation captures proteins that are in contact with the capture unit 30 minutes after the capture units are introduced to the sample preparation. Initiating the reaction freezes the proteins that transiently interact with the capture units at the 30 minute time point along the entrance pathway. Since UV light has not been irradiated onto the other preparations, a reaction has not been initiated in the other preparations, so the capture units in those preparations continue along the entrance pathway. UV light is then irradiated onto the second sample preparation 60 minutes after the capture units have been introduced to the preparation. That initiates the reaction and causes the capture units in the second preparation to capture proteins that are in contact with the capture units 60 minutes after the capture units are introduced to the sample preparation. Initiating the reaction freezes the proteins that transiently interact with the capture units at the 60 minute time point along the entrance pathway. Since a reaction has not been initiated in the other preparations, the capture units in those preparations continue along the entrance pathway. UV light is then irradiated onto the third sample preparation 120 minutes after the capture units have been introduced to the preparation. That initiates the reaction and causes the capture units in the third preparation to capture proteins that are in contact with the capture units 120 minutes after the capture units are introduced to the sample preparation. Initiating the reaction freezes the proteins that transiently interact with the capture units at the 120 minute time point along the entrance pathway.

The reactions in the preparations can be halted by adding excess nucleophile, such as Tris or glycine, which outcompetes the proteins for reaction with the capture units. A rapid method that combines quenching the reaction and denaturing the proteins in preparation for gel electrophoresis is to add boiling sodium dodecyl sulfate polyacrylamide gel electrophoresis (SDS-PAGE) buffer, which contains both Tris and β-mercaptoethanol, and then boiling the solution for 5 minutes. The sample can then be directly analyzed by gel electrophoresis.

Once the protein/capture unit complexes have been formed, the cells in the preparations are lysed and the protein/capture unit complexes are isolated. Isolating may be by any separation technique known in the art. Exemplary isolation protocols include including precipitation, chromatography, dialysis or ultrafiltration. Precipitation is perhaps the simplest method for separating one type of macromolecule from another. For example, proteins can be selectively precipitated in the presence of acetone. Most purification methods, involve some form of chromatography whereby molecules in solution (mobile phase) are separated based on differences in chemical or physical interaction with a stationary material (solid phase). Gel filtration (also called size-exclusion chromatography or SEC) uses a porous resin material to separate molecules based on size; large molecules are excluded from the tiny internal spaces of the resin beads while small molecules enter the resin pores, resulting in a longer path through the column. In ion exchange chromatography, molecules are separated according to the strength of their overall ionic interaction with a solid phase material. By manipulating buffer conditions, molecules of greater or lesser ionic character can be bound to or dissociated from the solid phase material.

In certain embodiments, affinity purification (affinity chromatography) is used to isolate the protein/capture unit complexes. Affinity chromatography makes use of specific binding interactions between molecules. A particular ligand is chemically immobilized or coupled to a solid support so that when a complex mixture is passed over the column, those molecules having specific binding affinity to the ligand become bound. After other sample components are washed away, the bound molecule is stripped from the support, resulting in its purification from the original sample.

Affinity purification generally involves incubating a crude sample with the affinity support to allow the target molecule in the sample to bind to the immobilized ligand, and wash away nonbound sample components from the support. The target is then eluted (dissociated and recovered) from the immobilized ligand by altering the buffer conditions so that the binding interaction no longer occurs.

Ligands that bind to general classes of proteins (e.g., antibodies) or commonly used fusion protein tags (e.g., 6×His) are commercially available in pre-immobilized forms ready to use for affinity purification. Alternatively, more specialized ligands such as specific antibodies or antigens of interest can be immobilized using one of several commercially available activated affinity supports; for example, a peptide antigen can be immobilized to a support and used to purify antibodies that recognize the peptide.

Most commonly, ligands are immobilized or coupled directly to solid support material by formation of covalent chemical bonds between particular functional groups on the ligand (e.g., primary amines, sulfhydryls, carboxylic acids, aldehydes) and reactive groups on the support. However, indirect coupling approaches are also possible. For example, a GST-tagged fusion protein can be first captured to a glutathione support via the glutathione-GST affinity interaction and then secondarily chemically crosslinked to immobilize it. The immobilized GST-tagged fusion protein can then be used to affinity purify binding partner(s) of the fusion protein.

Most affinity purification procedures involving protein: ligand interactions use binding buffers at physiologic pH and ionic strength, such as phosphate buffered saline (PBS). This is especially true when antibody:antigen or native protein: protein interactions are the basis for the affinity purification. Once the binding interaction occurs, the support is washed with additional buffer to remove nonbound components of the sample. Nonspecific (e.g., simple ionic) binding interactions can be minimized by adding low levels of detergent or by moderate adjustments to salt concentration in the binding and/or wash buffer. Finally, elution buffer is added to break the binding interaction and release the target molecule, which is then collected in its purified form. Elution buffer can dissociate binding partners by extremes of pH (low or high), high salt (ionic strength), the use of detergents or chaotropic agents that denature one or both of the molecules, removal of a binding factor or competition with a counter ligand. In most cases, subsequent dialysis or desalting is required to exchange the purified protein from elution buffer into a more suitable buffer for storage or downstream analysis.

The most widely used elution buffer for affinity purification of proteins is 0.1M glycine.HCl, pH 2.5-3.0. This buffer effectively dissociates most protein:protein and antibody:antigen binding interactions without permanently affecting protein structure. However, some antibodies and proteins are damaged by low pH, so eluted protein fractions should be neutralized immediately by addition of 1/10th volume of alkaline buffer such as 1M Tris.HCl, pH 8.5. Other elution buffers for affinity purification of proteins are listed in Table 1.

TABLE 1

Common elution buffers systems for protein affinity purification.

| Condition | Buffer |
|---|---|
| pH | 100 mM glycine•HCl, pH 2.5-3.0 |
| | 100 mM citric acid, pH 3.0 |
| | 50-100 mM triethylamine or triethanolamine, pH 11.5 |
| | 150 mM ammonium hydroxide, pH 10.5 |
| Ionic strength and/or chaotropic effects | 3.5-4.0M magnesium chloride, pH 7.0 in 10 mM Tris |
| | 5M lithium chloride in 10 mM phosphate buffer, pH 7.2 |
| | 2.5M sodium iodide, pH 7.5 |
| | 0.2-3.0 sodium thiocyanate |
| Denaturing | 2-6M guanidine•HCl |
| | 2-8M urea |
| | 1% deoxycholate |
| | 1% SDS |
| Organic | 10% dioxane |
| | 50% ethylene glycol, pH 8-11.5 (also chaotropic) |
| Competitor | >0.1M counter ligand or analog |

A support or matrix in affinity purification is any material to which a biospecific ligand is covalently attached. Typically, the material to be used as an affinity matrix is insoluble in the system in which the target molecule is found. Usually, but not always, the insoluble matrix is a solid. Useful affinity supports are those with a high surface-area to volume ratio, chemical groups that are easily modified for covalent attachment of ligands, minimal nonspecific binding properties, good flow characteristics and mechanical and chemical stability.

Immobilized ligands or activated affinity support chemistries are available for use in several different formats from Thermo Scientific. Most commonly, crosslinked beaded agarose or polyacrylamide resins are used for column- or small-scale purification procedures. Magnetic particles to which affinity ligands have been immobilized are especially useful for cell separations and certain automated purification procedures. Even polystyrene microplates, more commonly used for assay purposes, can be used as the support for immobilizing ligands to purify binding partners.

Porous gel supports generally provide the most useful properties for affinity purification of proteins. These types of supports are usually sugar- or acrylamide-based polymer resins that are produced in solution (i.e., hydrated) as 50-150 µm diameter beads. The beaded format allows these resins to be supplied as wet slurries that can be easily dispensed to fill and "pack" columns with resin beds of any size. The beads are extremely porous and large enough that biomolecules (proteins, etc.) can flow as freely into and through the beads as they can between and around the surface of the beads. Ligands are covalently attached to the bead polymer (external and internal surfaces) by various means. The result is a loose matrix in which sample molecules can freely flow past a high surface area of immobilized ligand.

In certain embodiments, the matrix is crosslinked beaded agarose, which is typically available in 4% and 6% densities. (This means that a 1 ml resin-bed is more than 90% water by volume.) Other matrices include polyacrylamide-based, beaded resin called ULTRALINK BIOSUPPORT (polyacrylamide-based gel, Thermo Scientific).

In other embodiments, the affinity purification is conducted using magnetic particles. Their small size provides the sufficient surface area-to-volume ratio needed for effective ligand immobilization and affinity purification. Magnetic beads are produced as superparamagnetic iron oxide particles that are covalently coated with silane derivatives. The coating makes the beads inert (i.e., to minimize nonspecific binding) and provides the particular chemical groups needed for attaching ligands of interest.

Affinity purification with magnetic particles is not performed in-column. Instead, a few microliters of beads is mixed with several hundred microliters of sample as a loose slurry. During mixing, the beads remain suspended in the sample solution, allowing affinity interactions to occur with the immobilized ligand. After sufficient time for binding has been given, the beads are collected and separated from the sample using a powerful magnet. Typically, simple bench-top procedures are done in microcentrifuge tubes, and pipetting or decanting is used to remove the sample (or wash solutions, etc.) while the magnetic beads are held in place at the bottom or side of the tube with a suitable magnet.

In certain embodiments, the capture unit further includes a handle that facilitates isolation of the protein/capture unit complexes by affinity purification. The handle is a chemical moiety that does not bind the proteins in the sample, and remains unreactive in the presence of light or chemicals used to initiate the reactions between the capture unit and the proteins in the sample. In an exemplary embodiment, the handle includes aldehyde group. The protein/capture unit complexes and remaining components of the sample are introduced to 30 µL of hydrazide affinity gel. The aldehyde group reacts with the hydrazide affinity gel, retaining the protein/capture unit complexes in the gel, while remaining components of the sample preparations pass through and out of the gel, thereby isolating the protein/capture unit complexes. In such an embodiment, strong wash conditions (e.g. 2% SDS 95° C. boiling 5 min, 8M urea 37° C. heating 10 min and 3M NaCl washing) to elute the protein/capture unit complexes from the gel.

In certain embodiments, the capture unit further includes a detectable label, such as an optically detectable label, such as a fluorescent label. The detectable label allows tracing of the capture unit with fluorescent imaging technologies or flow cytometry.

In certain embodiments, the detectable label is a fluorescent label. Suitable fluorescent labels include, but are not limited to, 4-acetamido-4'-isothiocyanatostilbene-2,2' disulfonic acid; acridine and derivatives: acridine, acridine isothiocyanate; 5-(2'-aminoethyl)aminonaphthalene-1-sulfonic acid (EDANS); 4-amino-N[3-vinylsulfonyl)phenyl] naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine.

The fluorescent label may be obtained commercially (e.g., from NEN DuPont, Amersham, and BDL). Methods for producing fluorescently labeled biological structures are known in the art, such as those described in Kambara et al. (Bio/Technol., 6:816-21, 1988); Smith et al. (Nucl. Acid Res., 13:2399-2412, 1985); and Smith et al. (Nature, 321: 674-679, 1986). The fluorescent dye may be linked to the member by a linker arm that is easily cleaved by chemical or enzymatic means. There are numerous linkers and methods for attaching labels to biological structures, as shown in Oligonucleotides and Analogues: A Practical Approach (IRL Press, Oxford, 1991); Zuckerman et al. (Polynucleotides Res., 15: 5305-5321, 1987); Sharma et al. (Polynucleotides Res., 19:3019, 1991); Giusti et al. (PCR Methods and Applications, 2:223-227, 1993); Fung et al. (U.S. Pat. No. 4,757,141); Stabinsky (U.S. Pat. No. 4,739,044); Agrawal et al. (Tetrahedron Letters, 31:1543-1546, 1990); Sproat et al. (Polynucleotides Res., 15:4837, 1987); and Nelson et al. (Polynucleotides Res., 17:7187-7194, 1989). Extensive guidance exists in the literature for derivatizing fluorophore and quencher molecules for covalent attachment via common reactive groups that may be added to a biological structure. Many linking moieties and methods for attaching fluorophore moieties to biological structures also exist, as described in Oligonucleotides and Analogues, supra; Guisti et al., supra; Agrawal et al, supra; and Sproat et al., supra.

One isolated, the proteins are dissociated from the capture units. In certain embodiments, the dissociation occurs by cleaving the reactive functional group, thereby dissociating the captured proteins from capture units. Any other method of breaking chemical bonds that does not harm the proteins may be used with methods of the invention.

The isolated proteins are then analyzed, which provides an analysis of the entrance pathway used by the member. Any method known in the art may be used to analyze the proteins. Exemplary analysis methods include SDS-PAGE in conjunction with Western blot, immunoprecipitation or co-immunoprecipitation and mass spectrometry.

In certain embodiments, liquid chromatography-mass spectrometry (LC-MS) is used to analyze the isolated proteins. The work-flow for preparing proteins for LC-MS is well known in the art. Such a workflow is described, for example in Gundry et al. (Curr Protoc Mol. Biol. 2009; Chapter 10), the content of which is incorporated by reference herein its entirety. Briefly, the protein is first broken up into peptides, either by chemical or enzymatic digestion, prior to MS analysis. The MS analysis is performed on the individual peptides, and the information is then stitched together to reveal the protein identity and/or characteristics (e.g., co- and post-translational modifications or isoforms). Important steps in this strategy include the preparation of the protein sample for digestion, enrichment for any particular peptides of interest, and cleanup or desalting of the final peptide mixture prior to MS analysis. Gundry also provides methods for preparing proteins for MS analysis after affinity purification.

While methods of the invention may be used to analyze any molecular interactions and any cell entry pathways, methods of the invention are particularly useful for analyzing viral entry into cells. Viral populations do not grow through cell division, because they are acellular. Instead, they use the machinery and metabolism of a host cell to produce multiple copies of themselves, and they assemble in the cell. The life cycle of viruses differ greatly between species but there are six basic stages in the life cycle of viruses. The first stage is attachment, which is a specific binding between viral capsid proteins and specific receptors on the host cellular surface. This specificity determines the host range of a virus. Attachment to the receptor can induce the viral envelope protein to undergo changes that results in the fusion of viral and cellular membranes, or changes of non-enveloped virus surface proteins that allow the virus to enter. The second stage is penetration follows attachment, in which virions enter the host cell through receptor-mediated endocytosis or membrane fusion. This is often called viral entry. The infection of plant and fungal cells is different from that of animal cells. Plants have a rigid cell wall made of cellulose, and fungi one of chitin, so most viruses can get inside these cells only after trauma to the cell wall. The third stage is uncoating, in which the viral capsid is removed. This may be by degradation by viral enzymes or host enzymes or by simple dissociation. The end-result is the releasing of the viral genomic nucleic acid. The fourth stage is replication of viruses, which involves primarily multiplication of the genome. Replication involves synthesis of viral messenger RNA (mRNA) from early genes, viral protein synthesis, possible assembly of viral proteins, then viral genome replication mediated by early or regulatory protein expression. This may be followed, for complex viruses with larger genomes, by one or more further rounds of mRNA synthesis: late gene expression is, in general, of structural or virion proteins. The fifth stage is structure-mediated self-assembly of the virus particles. In this stage, some modification of the proteins often occurs. In the sixth and final stage, viruses can be released from the host cell by lysis, a process that kills the cell by bursting its membrane and cell wall if present. Methods of the invention may be used to capture and isolate the various cellular proteins that interact with a virus as it goes through the above process.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

The Examples below illustrate a novel proteomics approach to identify interacting proteins at different delivery time points by using engineered PAMAM dendrimers and mass spectrometry identification methods. The engineered dendrimers were designed and synthesized in-house to enable cross-linking of a dendrimer with proteins on its delivery path and isolation of the cross-linked proteins. The labeling reaction and affinity purification of these interacting proteins are demonstrated and optimized with in vitro labeling experiments. The in vivo delivery of engineered dendrimers is demonstrated by using flow cytometry approach. Proteins that interact with dendrimers in vivo were purified and identified from two delivery time points. Two different engineered dendrimers are compared, one of which contains a cell penetrating peptide to help cross-membrane transportation. The proteomics approach is un-biased, high throughput and can reveal molecular level information of cells under their native conditions. Therefore the development of the approach described herein improves the understanding of not only dendrimers, but also other nanoparticles or viruses delivery mechanisms. Other biomedical delivery cargos can be similarly synthesized using this approach and the same proteomics analyses can be employed to visualize their delivery pathways in vivo.

Example 1

Materials

Polyamidoamine dendrimer generation 3 (PAMAM G3), HOBt (hydroxybenzotriazole), DIPCI (1,3-diisopropyl carbodiimide), FITC (Fluorescein isothiocyanate), BMPA (3-Maleimidopropionic acid N-(2-Carboxyethyl)maleimide), 2-ME (2-Mercaptoethanol), NP40 (Tergitol) were purchased from Sigma-Aldrich (St. Louis, Mo.). NHS-SS-Diazirine (cPL) and NHS-LC-Diazirine (PL), Sodium meta-Periodate (NaIO4) and SNAKESKIN pleated dialysis tubing (dialysis tubing; 3,500 MWCO, 22 mm dry diameter, Thermo Scientific) were purchased from Pierce (Rockford, Ill., USA). Materials were used directly without purification.

Example 2

Dendrimer Synthesis

Fifty-two microliters of PAMAM G3 (1.3 µmol) were dried under vacuum and then redissolved in 500 µL DMSO. A mixture of 5.2 µmol BMPA and 3.9 µmol HOBt was dissolved in 500 µL DMOS. A solution of 3.9 µmol of DIPCI was added to and the mixture was incubated for 30 min. Then the PAMAM solution was added to this mixture and reacted to BMPA at room temperature overnight. The reaction solution was dialyzed against a DMSO and water (1:4) mixture and then substantially pure water to remove any excess reagent. The solution was then dried under vacuum and re-dissolved in 500 µL DMSO. Cleavable and non-cleavable photoreactive labeling reagents (cPL and PL), NHS-SS-Diazirine and NHS-LC-Diazirine were used in the synthesis of dendrimers suitable for the in vitro and in vivo experiments, respectively. In both cases, 5.2 µmol of PL or cPL were dissolved in 500 µL DMSO and incubated 4 hours with the dendrimer solutions in dark. Then 2.6 µmol of imaging reagent FITC was dissolved in 50 µL DMSO and incubated with the mixture overnight in dark. The reaction mixture was dialyzed again remove excess reagent. Two handles PEG and MAP were used in two synthesis routes of dendrimers that have different internalization rates. Both of the handles have a sulfhydryl group on one end, which reacted to the maleimide group that was coupled to the dendrimer in the first synthesis step. The reaction happened under neutral or mild acidic conditions; therefore the dialyzed product was mixed with a 10×PBS solution to make the final solution in neutral pH.

Then 2.6 µmol PEG and MAP handles were added respectively to dendrimer solutions and incubated for 2 hours at room temperature in dark. Then 13 µmol of 2-ME was added to the reaction mixture to block any maleimide group that did not react with the handle reagents. The reaction mixture was then dialyzed against water overnight in dark. The other end of the handle reagents can be oxidized to produce an aldehyde group, which enables affinity purification via an aldehyde-hydrazide reaction. Therefore, the dendrimer product was oxidized in a solution with a final concentration of 20 mM $NaIO_4$ for 1 hour. Then the reaction mixture was dialyzed against water in dark overnight to purify the final product. The final product was stored at 4° C. for further use.

Example 3

Cell Culturing

DG-75 and Hela cells were grown in RPMI-1040 and DMEM media substituted with 10% inactivated FBS, 1% sodium pyruvate, 0.5% streptomycin/penicillin, and 0.05% 2-ME in 5% CO2 at 37° C., respectively.

Example 4

In Vitro Labeling

One hundred microliters of DG-75 cell pellets were collected, washed with cold PBS 3 times and lysed in 1 mL solution of 1% NP40/PBS with sonication. The sonication was kept on for 10 s and off for 20 s, and the cycle was repeated 5 times. Then the protein mixture was separated from the cell debris by centrifuging the solution at 15,000 G for 10 min. BCA quantitation was used to measure the protein concentration in the supernatant. One hundred micrograms of DG-75 cell lysate was mixed with 15 pmol of G3-FITC,PEG and G3-FITC,cPL,PEG as control and experimental samples, respectively. The control sample was kept in dark, while the experimental sample was irradiated under UV light for 10 min to enable labeling via photo-activation. Then 30 µL of hydrazide affinity gel was washed and added to each of the two samples, respectively. The mixtures were rotated in dark for 2 hours at 4° C. Then the affinity beads were separated from the supernatant by microcentrifuging.

The beads were washed with 300 μL solutions of 1% NP40/PBS and 3M NaCl, respectively. Then the beads were mixed with 30 μL LDS sample buffer and heated at 95° C. for 5 min. The LDS sample buffer contained 1×LDS and 20 mM DTT to cleave the disulfide bond in cPL to release the labeled proteins. The eluted proteins were visualized on a 12% SDS-PAGE gel. Five, ten and fifteen minutes of UV irradiation were tested to optimize the labeling efficiency. The sample preparation steps followed those described in the last paragraph and the difference is the UV irradiation time length. In addition, the following washing solutions were used to remove the non-labeled proteins: 1% NP40/H$_2$O; 8M urea in Tris-HCl, pH 8.5; 2% SDS, 50 mM EDTA in Tris-HCl, pH 7; 3M NaCl in H$_2$O; 50 mM Glycine in H$_2$O, pH 4 and 80% acetonitrile, 0.1% TFA in H2O. The other sample preparation steps were the same as described earlier, except that these washing solutions were used separately to test their washing power individually.

Example 5

In vivo labeling

Dendrimers modified with non-cleavable photo-reactive labeling reagent (PL) were used in the in vivo labeling experiments because of the reducing environment inside live cells. In addition, dendrimer delivery was monitored with flow cytometry using the coupled FITC group. A final concentration of 5 μM of dendrimers G3-FITC,PL,PEG and G3-FITC,PL,MAP were added to Hela cell culture media respectively and approximately 105 cells were grown in these media up to 6 hours. Cells were collected and fixed at 2, 4 and 6 hours, respectively and the FITC fluorescence was measured at each time point for the two different dendrimers. The detailed cells collection and fixation method is as following. After dendrimer internalization, the media was removed and cells were washed 3 times with PBS to remove free extracellular reagents. Then the cells were digested with trypsin and collected from the culture dishes. The collected cells were washed another time with PBS and fixed with 250 μL fixation buffer at 4° C. for 15 min. The fixation buffer contained 0.1 g paraformaldehyde powder in PBS. Then the cells were washed another 3 times to remove the fixation buffer and the fluorescence of 10,000 Hela cells was measured on an Accuri C6 flow cytometer (Accuri, Ann Arbor, Mich.).

In vivo labeling experiments for mass spectrometry analyses were performed with 5 μM dendrimers as well. Take the PEG-handle dendrimers as an example, G3-FITC,PEG and G3-FITC,PL,PEG were added to the culture media of two plates of Hela cells as control and experimental samples, respectively. Approximately $10^7$ Hela cells were cultured in these two media for 30 min and 6 hours in dark, respectively. Then the media in the experimental sample was removed, the cells were washed 3 times with PBS, and 5 mL of Hela cell culture media without dendrimer was added back to cells. Then the cells were irradiated under UV light for 10 min on top of ice to reduce heat generated from UV irradiation. At the same time, the control cells were kept in dark. Both the two plates of cells were then washed 3 times with PBS, trypsin digested, collected and washed another 3 times with PBS. The cell lysis and affinity purification methods were the same as those described in the in vitro experiment part. The beads were washed with 3M NaCl, boiled at 95° C. with 2% SDS and heated at 37° C. with 8M urea. A solution of 300 μL of each washing solution was used, and the washing steps were repeated 3 times with each solution. The beads were further washed 3 times with 300 μL of 100 mM NH$_4$HCO$_3$ solutions to remove the earlier washing solutions. Proteins captured on the affinity beads were reduced and alkylated with 10 mM TCEP for 15 min and 20 mM IAA for 30 min in NH$_4$HCO$_3$, respectively; and then digested with trypsin at 37° C. overnight with a trypsin:protein ratio of 1:100. The digested peptide samples were de-salted with Sep-Pak columns (Waters, Milford, Mass.) and subjected to LC-MS/MS analyses. The de-salting method followed the product instruction of Sep-Pak columns. Biological triplicated samples were prepared for both the two delivery time points.

For dendrimers with the MAP-handle, the same sample preparation methods were used, except that the PEG-dendrimers were replaced by the MAP-dendrimers, e.g. G3-FITC,MAP (control) and G3-FITC,PL,MAP (experimental). Again, biological triplicated samples were prepared to obtain high confidence of the identification results.

Example 6

Mass Spectrometry Analyses

The peptide samples were dried under vacuum after de-salting and re-dissolved in 20 μL of 0.1% formic acid in H2O. Eight microliters of the solution was injected into an Eksigent NanoLC Ultra 2D system. A 30-cm long C18 column with 75 μm i.d. was packed in-house with 5 μm C18 Magic beads resin. The mobile phase buffer A constituted 0.1% formic acid in ultra-pure water, and buffer B contained 0.1% formic acid in acetonitrile. The following gradient was used in the LC-MS/MS experiment: the gradient changed from 2% to 40% buffer B within 90 min; then it was increased to 80% of buffer B within 1 min and washed the column for 5 min. At the end, the gradient was reduced back to 2% of buffer B and the column was equilibrated for 15 min. The flow rate of HPLC was 300 mL/min. The electrospray ionization emitter tip was generated on the pre-packed column with a laser puller (Model P-2000, Sutter Instrument Co.). The Eksigent Ultra2D HPLC system was coupled online with a high resolution hybrid linear ion trap orbitrap mass spectrometer (LTQ-Orbitrap Velos; Thermo Fisher). The mass spectrometer was operated in the data-dependent mode in which a full-scan MS (from m/z 300-2000 with the resolution of 30,000) was followed by 20 MS/MS scans of the same abundant ions. Ions with unassigned charge state were excluded. The mass exclusion time was set as 15 s.

Example 7

Database Search

The collected LC-MS/MS data were searched against IPI human database (v.3.64) with no redundant entries using SEQUEST algorithm on Proteome Discoverer (Version 1.2; Thermo Fisher). The following parameters were used: peptide precursor mass tolerance was set to 10 ppm; MS/MS tolerance was 0.8 Da; a static modification of cysteine alkylation (+57.0214 Da) and a variable modification of methionine oxidation (+15.9949 Da) were allowed; the digestion enzyme was specified as trypsin and a maximum of two missed cleavages were allowed. Search results with a false discovery rates (FDR) no more than 0.01 were reported as identified peptides.

Example 8

Engineered Dendrimers

Several engineered dendrimers were synthesized from the backbone of G3 PAMAM dendrimer in house (FIG. 1A). In general, the engineered dendrimers have a photo-reactive labeling functional group, a handle to enable affinity purification and an imaging functional group to allow light microscopy and flow cytometry experiments. The imaging group used in these experiments was FITC.

Figure 1B:
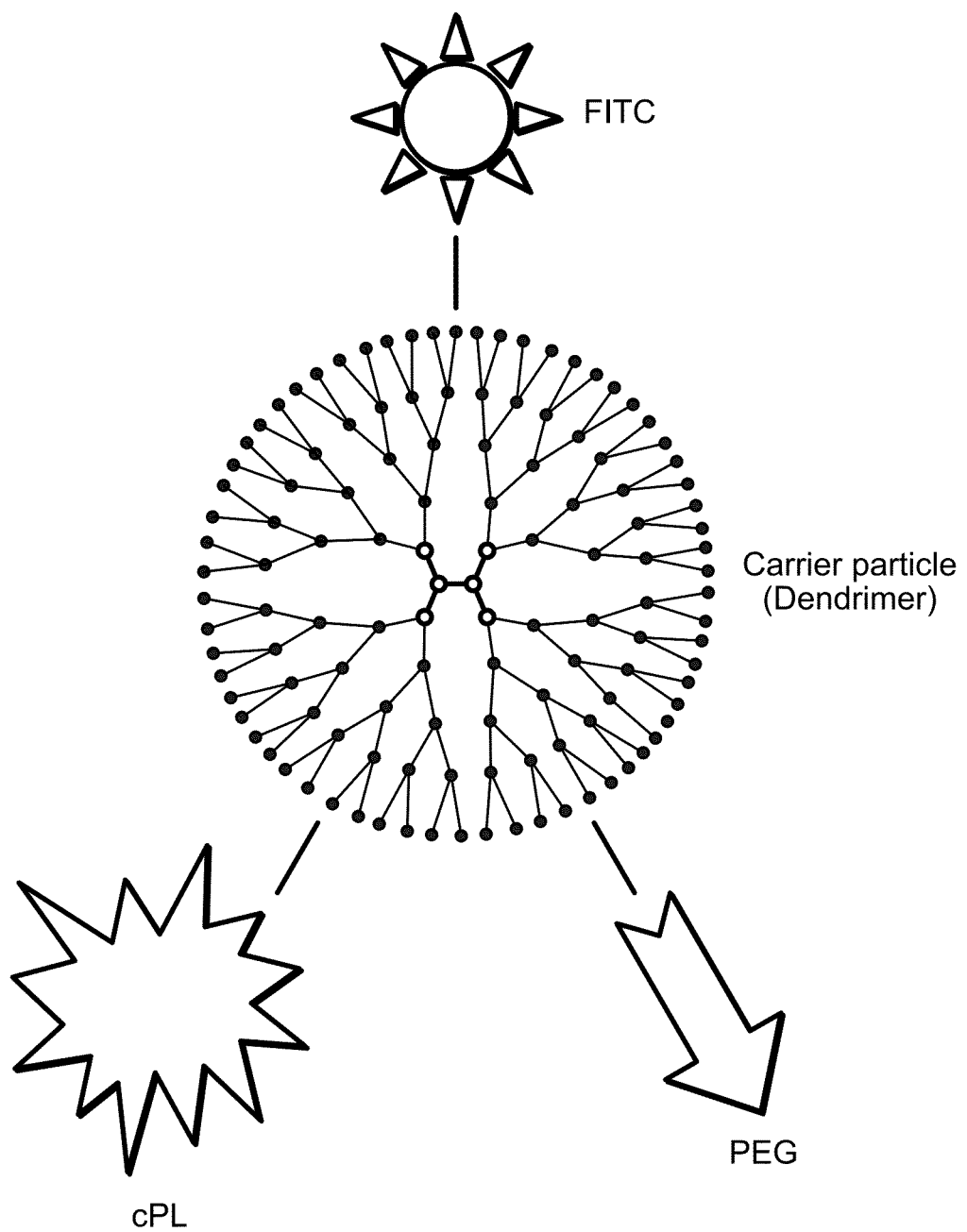
FIG. 1B is a diagram showing an engineered dendrimer used in the in vitro experiment. A fluorescent group FITC, a cleavable photo-reactive labeling group cPL and a handle containing a polyethylene glycol (PEG) moiety were coupled to a PAMAM Generation 3.0 backbone.

Several different dendrimers were synthesized to serve different purposes. For example, in order to visualize the labeled proteins on an SDS-PAGE gel, the labeled proteins may need to be cleaved off from dendrimers before being loaded on a gel. Therefore a cleavable photoreactive labeling group (cPL) was used (FIG. 1B). The general structure for a cleavable photoreactive labeling group is:

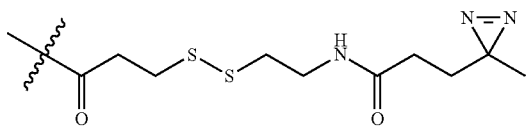 [SMILES: *C(=O)CCSSCCNC(=O)CCC1(C)N=N1]

Figure 1C:
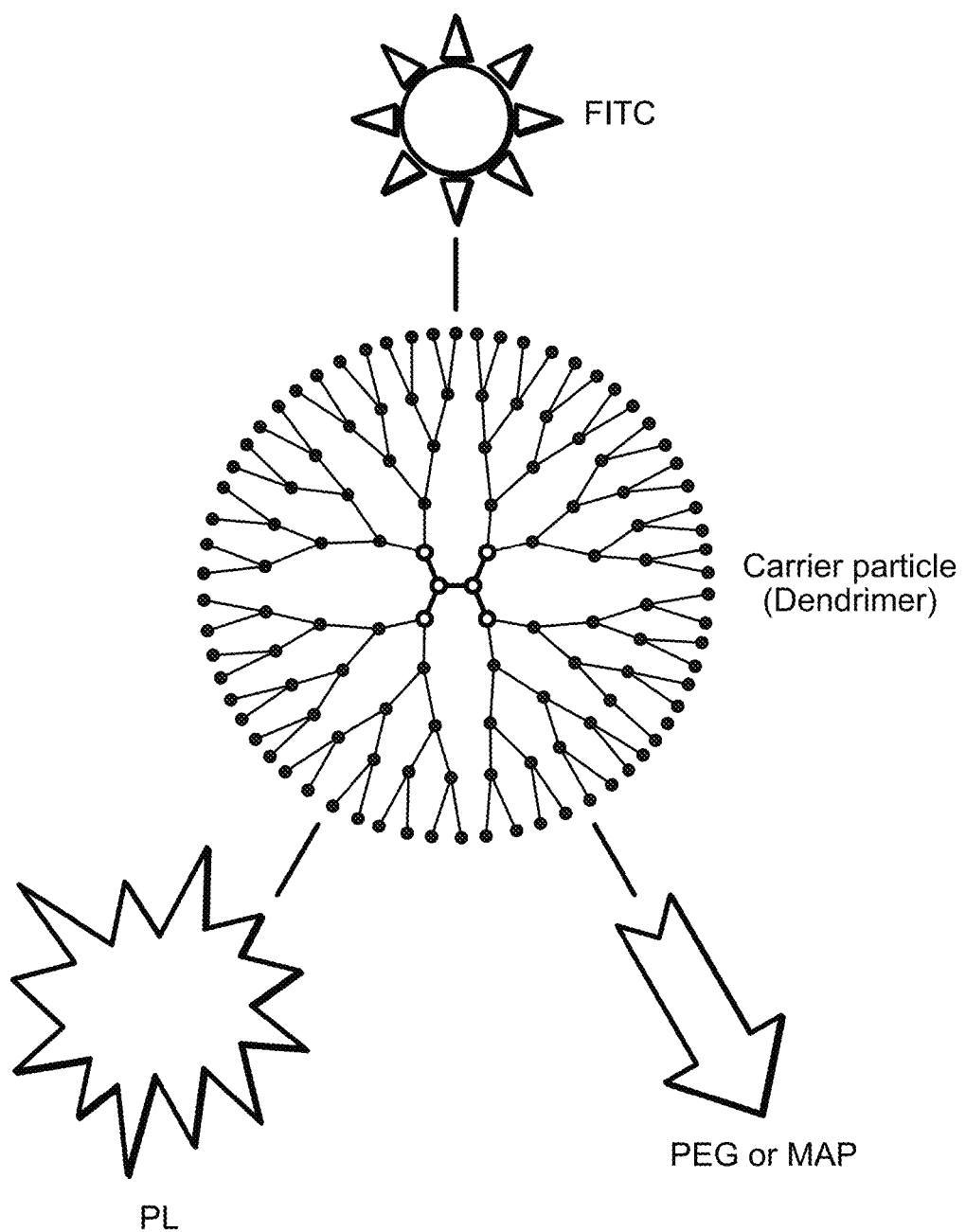
FIG. 1C is a diagram showing an engineered dendrimer used in the in vivo experiments. Similar to the one used in the in vitro experiments, FITC was employed as the fluorescent reagent. A non-cleavable photo-active labeling group PL was coupled to PAMAM G3.0 dendrimers for the in vivo experiments because of the reducing environment inside live cells. Two different handles were added respectively: one is the same PEG handle as the one used in the in vitro experiments; and the other contained a cell penetrating peptide MAP to enable highly efficient dendrimer internalization.

However, the disulfide bond in cPL will be reduced in live cells, thus in the in vivo experiments, dendrimers with non-cleavable labeling reagent PL were used (FIG. 1C). The general structure for a noncleavable photoreactive labeling group is:

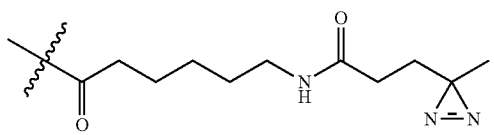 [SMILES: *C(=O)CCCCCNC(=O)CCC1(C)N=N1]

In addition, the trans-membrane delivery efficiency depends on the physical properties of the dendrimer and the coupled functional groups. The basic functional role of the handle group is to enable affinity purification, but other desired properties can also be added. For example, here two different handles (FIG. 1C, PEG (polyethylene glycol) and MAP) were coupled to dendrimers respectively, which resulted in different delivery rates, because MAP is a known cell penetrating peptide (cpp) that helps internalization of drugs, peptides and proteins. The structure for PEG and Map are shown below.

Example 9

Mass Spectrometry Approach to Trace Dendrimer Delivery

Figure 2:
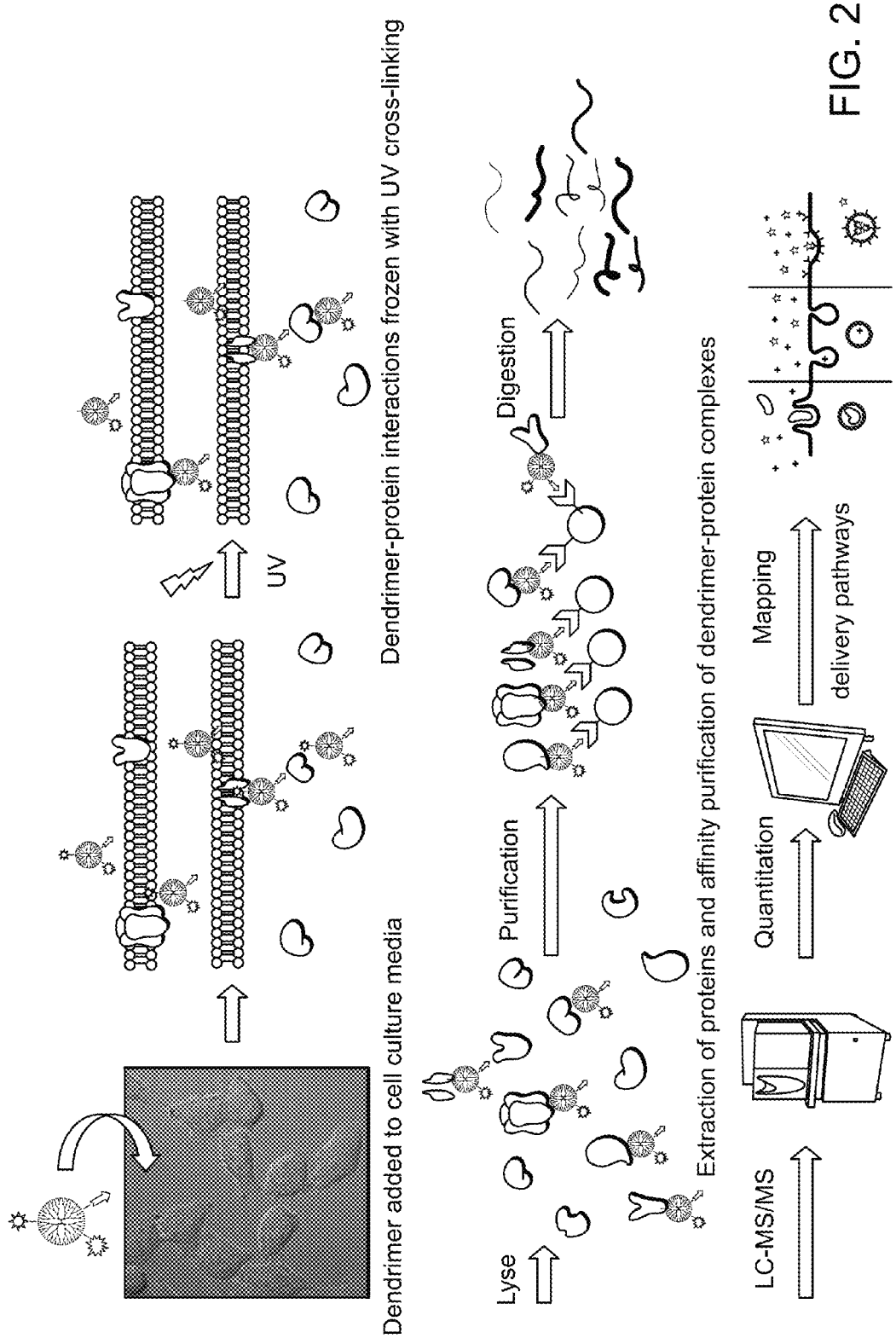
FIG. 2 is a diagraph showing a proteomics approach to trace dendrimer delivery. In general, the process contains internalization of engineered dendrimers into live cells, ultra violet (UV) irradiation to cross-link dendrimers with interacting proteins, enrichment of the interacting proteins and identification of proteins with LC-MS/MS strategies.

A general work flow of the mass spectrometry approach to trace dendrimer delivery is shown in FIG. 2. The process contains internalization of engineered dendrimers into live cells, UV (ultra violet) irradiation to cross-link dendrimers with interacting proteins, enrichment of the cross-linked proteins and identification of proteins with LC-MS/MS strategies. In the later parts of this report, steps of this approach will be demonstrated.

Example 10

UV Irradiation Results in Protein Labeling

Figure 3:
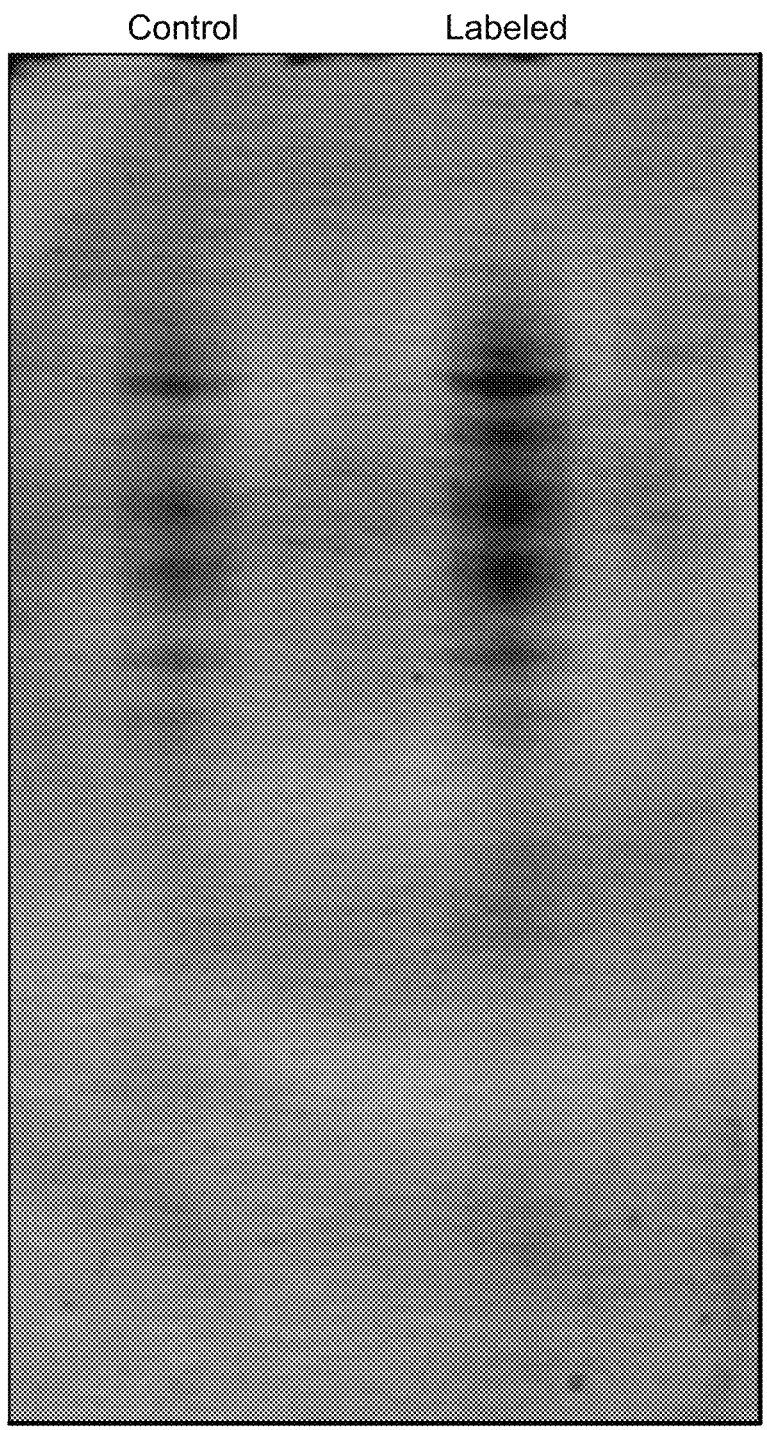
FIG. 3 is a photograph of a gel showing in vitro labeling of DG-75 cell lysate. The same amount of engineered dendrimers G3-FITC, PEG (control) and G3-FITC, cPL, PEG (experimental) was incubated with equal amount of DG-75 cell lysates. Proteins and dendrimers in the experimental sample were cross-linked under UV irradiation, while the control sample was kept in dark. Then the crosslinked protein-dendrimer complexes were purified using hydrazide affinity gel and the nonlabeled proteins were removed with washes. The labeled proteins were then eluted by cleaving the disulfide bond of cPL and visualized on an SDS-PAGE gel. A lot more proteins can be observed in the labeled sample than in the control sample, which indicates that labeling is enabled by UV irradiation.
Figure 4:
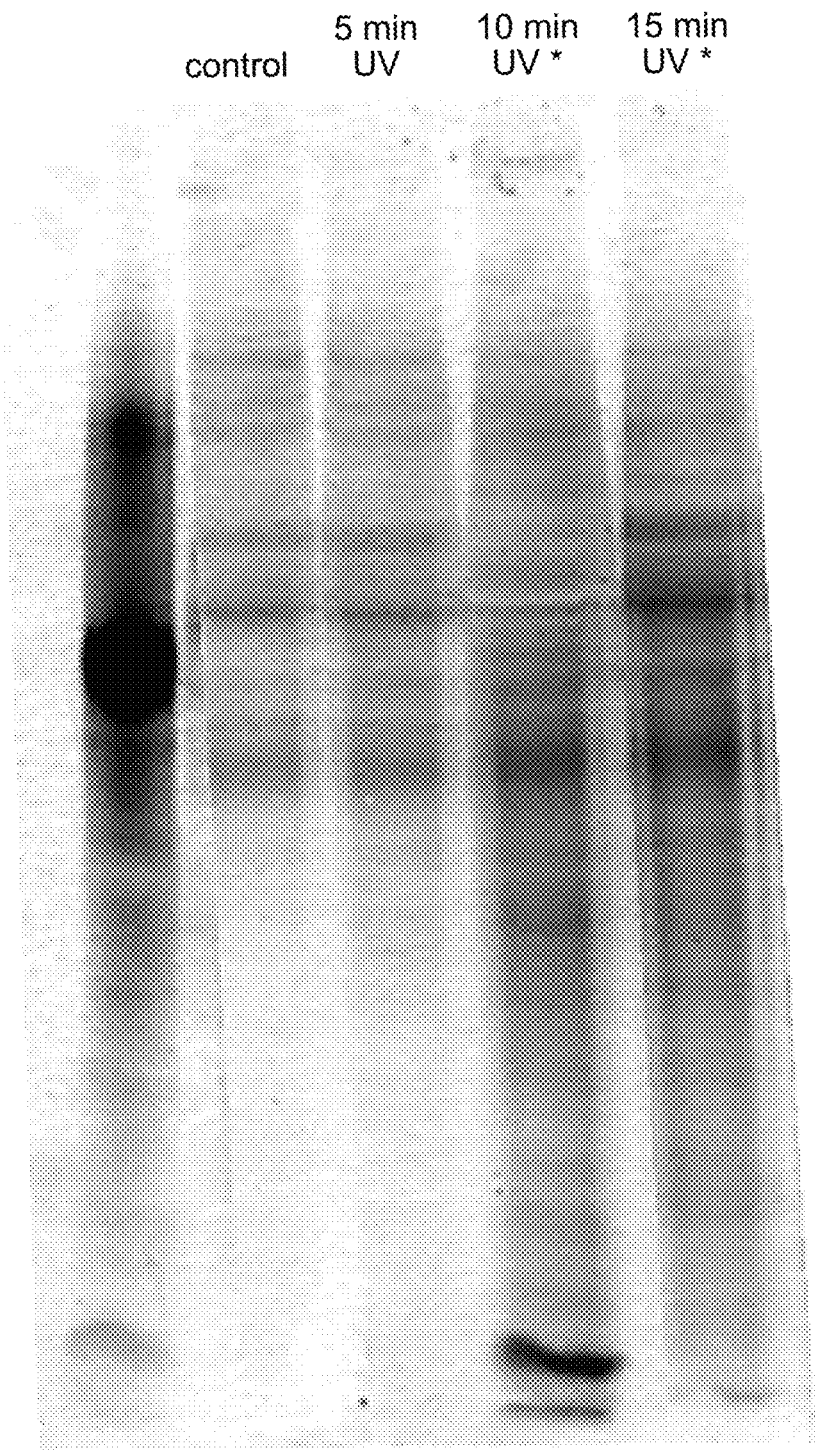
FIG. 4 is a photograph of a gel showing efficiency of the UV light cross-linking reaction. 10-15 minutes resulted in high cross-linking efficiency. Cross-linking was optimized by varying the UV irradiation time length. The same dendrimer-lysate mixtures were irradiated under UV light for 5-15 min and 10-15 minutes irradiation resulted in the highest cross-linking efficiency.

UV irradiation on the photo-reactive labeling group allows dendrimers to be cross-linked to the interacting proteins. The handles on the dendrimers contain an aldehyde group on the end, which covalently reacts to hydrazide affinity gel. Thus, dendrimers with their cross-linked proteins can be specifically purified from a protein mixture. The labeling reagent is sensitive to light, and it may result in false positive labeling when exposed to ambient light. Thus dendrimers without the labeling reagent were used as controls. Therefore the engineered dendrimers G3-FITC,PEG (control) and G3-FITC,cPL,PEG (experimental) were incubated with two aliquots of the same amount of DG-75 cell lysate; and the experimental sample was cross-linked under UV irradiation. Then the cross-linked protein-dendrimer complexes were purified using hydrazide affinity gel and the non-cross-linked proteins were removed with washes. The cross-linked proteins were then cleaved off from the hydrazide gel solid support by reducing the disulfide bond in cPL. The released proteins were visualized on an SDS-PAGE gel (FIG. 3), which shows that a lot more proteins are observed in the labeled sample than in the control sample. This observation demonstrated the cross-linking between engineered dendrimer and proteins under UV irradiation. Furthermore, the labeling efficiency depends on the UV irradiation time length. FIG. 4 shows that 10 to 15-minute of UV irradiation results in the highest labeling efficiency. Therefore in the later experiments, 10 min UV irradiation was used to achieve a high labeling efficiency and at the same time, to avoid cell death due to long time exposure to UV light.

Example 11

Affinity Purification Efficiency

The hydrazide affinity purification efficiency was tested by measuring the light absorbance of the imaging group FITC

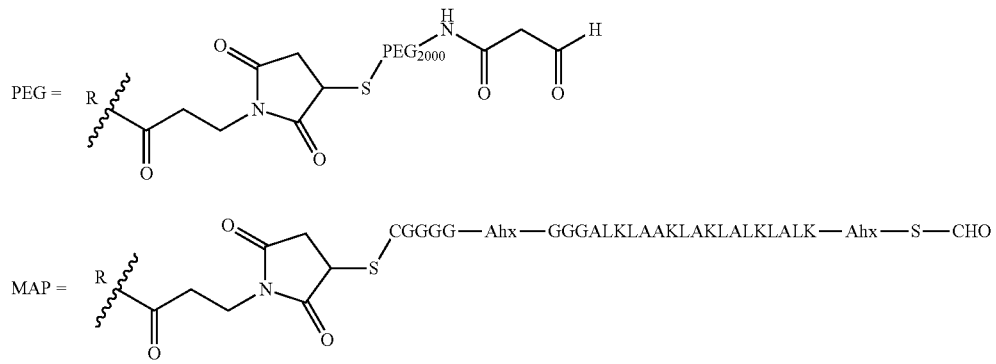

(peak absorbance at 490 nm) before and after purification. The efficiency was determined by Equation 1 below.

$$\text{Capture \%} = \frac{\text{Abs}_{490\,nm}(\text{before capture}) - \text{Abs}_{490\,nm}(\text{after capture})}{\text{Abs}_{490\,nm}(\text{before capture})} \times 100\%$$

Equation 1

Figure 5:
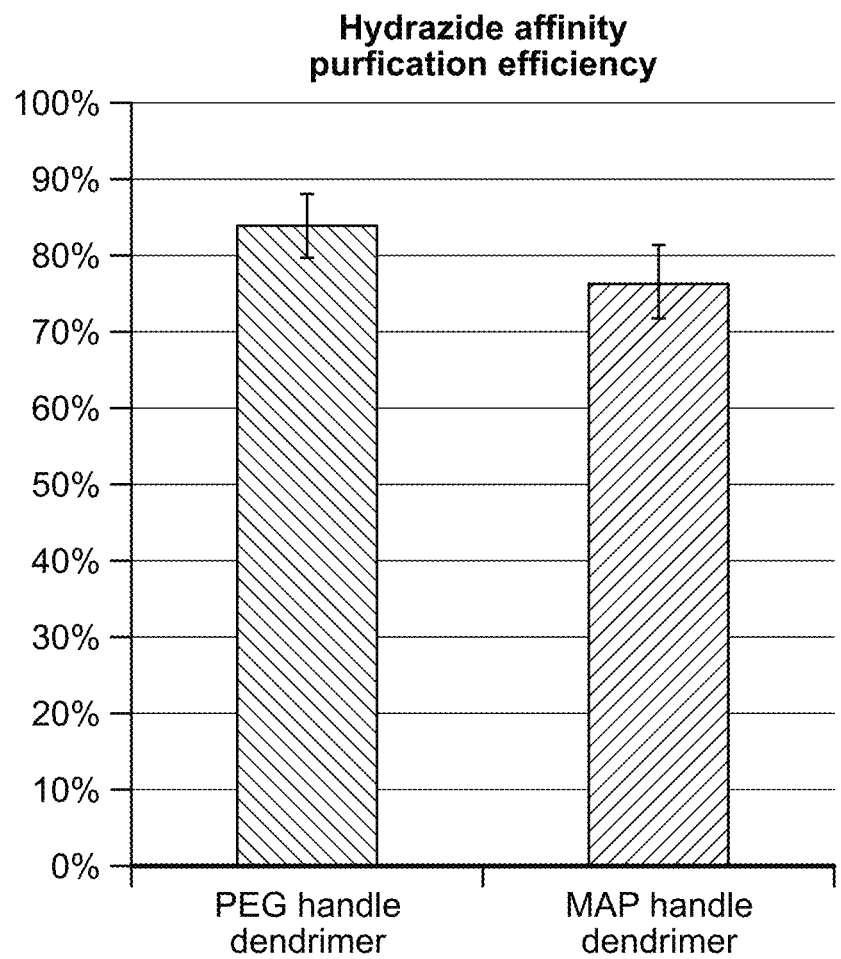
FIG. 5 is a graph showing affinity purification efficiency of two dendrimers with different handles, PEG and MAP. 75-85% purification efficiencies were observed for both dendrimers.

The result (FIG. 5) shows that the capture efficiency is approximately 75-85% in both the experiments with G3-FITC, PL,PEG and G3-FITC, PL,MAP dendrimers.

Example 12

Optimizing Washing Conditions

Figure 6:
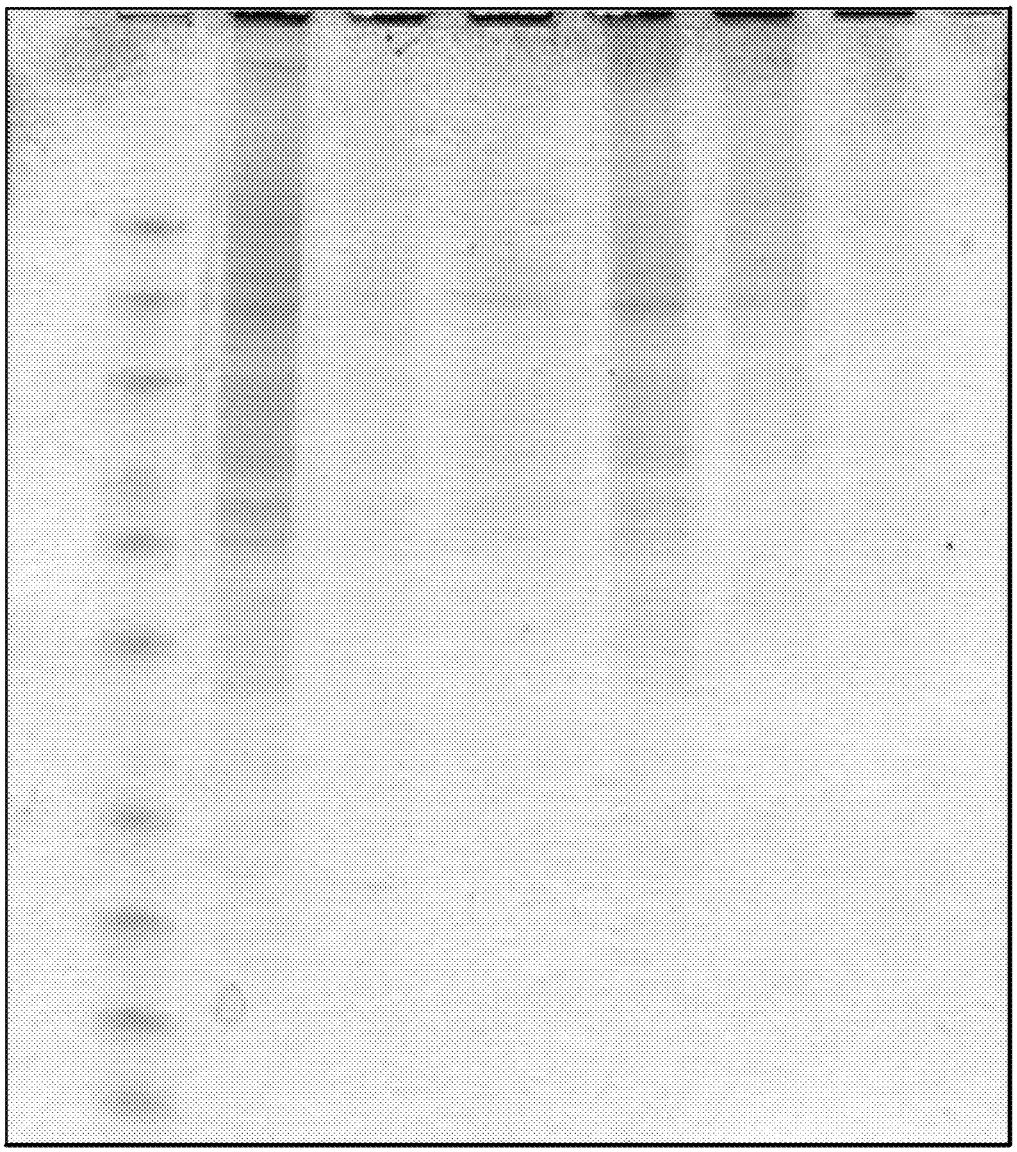
FIG. 6 is a photograph of a gel showing the results of testing several washing conditions to remove the majority of non-labeled proteins. Commonly used IP buffer (1% NP40 in Tris-HCl buffer), denaturing buffers (8M urea and 2% SDS), high concentration of salt solution (3M NaCl), low pH buffer (Glycine pH 4) and organic solution (80% acetonitrile and 0.1% TFA) were used in this experiment. The results show that 2% SDS, 8M urea and 3M NaCl washes are the most efficient.

An issue in the affinity purification coupled with mass spectrometry experiments is the removal of non-specific binding proteins. In this experiment, the specifically labeled proteins are covalently cross-linked to dendrimers, which are then covalently linked to the hydrazide affinity gel. Therefore washing conditions were employed to remove non-specific binding proteins, which is an aspect over other immunoprecipitation (IP) type proteomics studies. In FIG. 6, several washing conditions were tested, including commonly used IP buffer (1% NP40 in Tris-HCl buffer), denaturing buffers (8M urea and 2% SDS), high concentration of salt solution (3M NaCl), low pH buffer (Glycine pH 4) and organic solution (80% acetonitrile and 0.1% TFA). In the later experiments, 2% SDS, 8M urea and 3M NaCl washes were used based on results here.

Example 13

In Vivo Delivery and Labeling of Hela Cells

Dendrimers with non-cleavable labeling reagents G3-FITC,PL,PEG and G3-FITC,PL,MAP were added to Hela cell culture media respectively to a final concentration of 5 µM. Two plates of Hela cells were cultured in these media respectively; and then the cells were washed and fixed after 2, 4 and 6 hours of dendrimer delivery. The control sample was prepared using Hela cells grown without any dendrimer. Then the fluorescence in the fixed cells was measured with flow cytometry. It needs to be considered that these two dendrimers were synthesized separately with different synthesis routes. Therefore, these synthesis differences may need to be considered when analyzing the flow cytometry results. The dendrimer with the MAP handle had a lighter fluorescence than that with the PEG handle under the same condition. This observation is related to the oxidation step to generate an aldehyde group on the end of the MAP handle. Thus the reported raw flow cytometry absorbance values (FC) were normalized with the absorbance of the cell culture media (Abs) to correct any starting material differences. The normalization formula is shown below as Equation 2.

$$FC' = \frac{(FC_{dendrimer} - FC_{control})}{\text{Abs}_{490\,nm}(\text{media contains dendrimer})}$$

Equation 2

Figure 7:
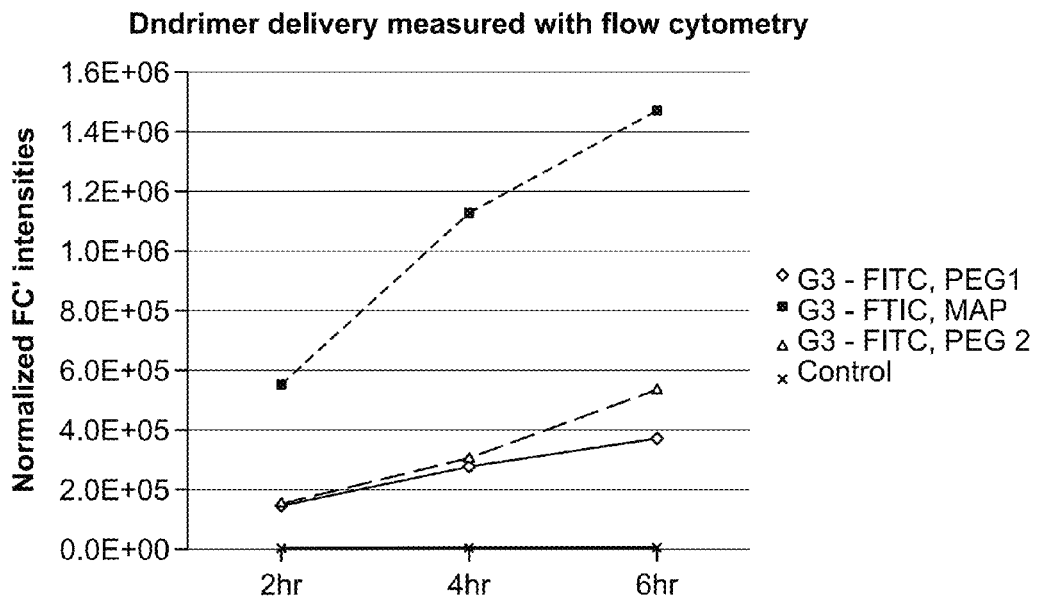
FIG. 7 is a graph showing in vivo dendrimer delivery monitored with flow cytometry. A final concentration of 5 µM of dendrimers G3-FITC,PL,PEG and G3-FITC,PL,MAP were added to the Hela cell culture media. Hela cells were cultured in these media for 6 hours, respectively. Cells were washed and fixed after 2, 4 and 6 hours. Dendrimer delivery was determined by measuring the FITC fluorescence in cells with a flow cytometer, because dendrimers contained FITC in their structures. The raw flow cytometry readings were normalized and plotted.

The normalized results are plotted in FIG. 7. Both of those two dendrimers were internalized efficiently within 2 hours, and the delivery was continued up to at least 6 hours (Data points after 6 hours were not collected). The delivery rate of G3-FITC,PL,MAP was approximately 5 times more than that of G3-FITC,PL,PEG; because MAP is known as a cell penetrating peptide, which helps internalization of medium to large size molecules (e.g. peptides, proteins).

Example 14

In Vivo Labeling and Identification of the Labeled Proteins with Mass Spectrometry Dendrimers G3-FITC, PEG; G3-FITC, MAP; G3-FITC, PL, PEG and G3-FITC, PL, MAP were added into Hela cell culture media to a final concentration of 5 µM, respectively. The two dendrimers without photo-reactive labeling reagents (G3-FITC,PEG and G3-FITC,MAP) were used as negative controls to avoid any false positive labeling. The other two dendrimers with labeling reagents (G3-FITC, PL, PEG and G3-FITC, PL, MAP) were used to cross-link dendrimers to interacting proteins. The delivery time points were determined with confocal microscopy and in the experiment described here. Two time points were used. Cells were grown in the media at 37° C. for 30 min and 6 hours respectively (the beginning and ending time points of delivery), and then washed to remove free dendrimers that were not binding to the membrane or delivered into cells. Then fresh cell culture media without dendrimers were added to cells, and the experimental samples were irradiated under UV light for 10 min to allow cross-linking. The control samples were kept in the dark during the whole process. Therefore four groups of samples were collected: two control samples and two labeled samples using two dendrimers with different handles. In addition, two time points (30 min and 6 hours) of delivery were allowed for each group of samples. In total, 8 different types of samples were prepared.

It is useful to have biological replications to further eliminate false positive identifications. Therefore 3 biological replicated samples were prepared for each of these 8 types of samples from culturing cells. In this experiment, no technique replicated samples were employed. The collected cells were lysed and purified as reported in the in vitro experiments.

Figure 8:
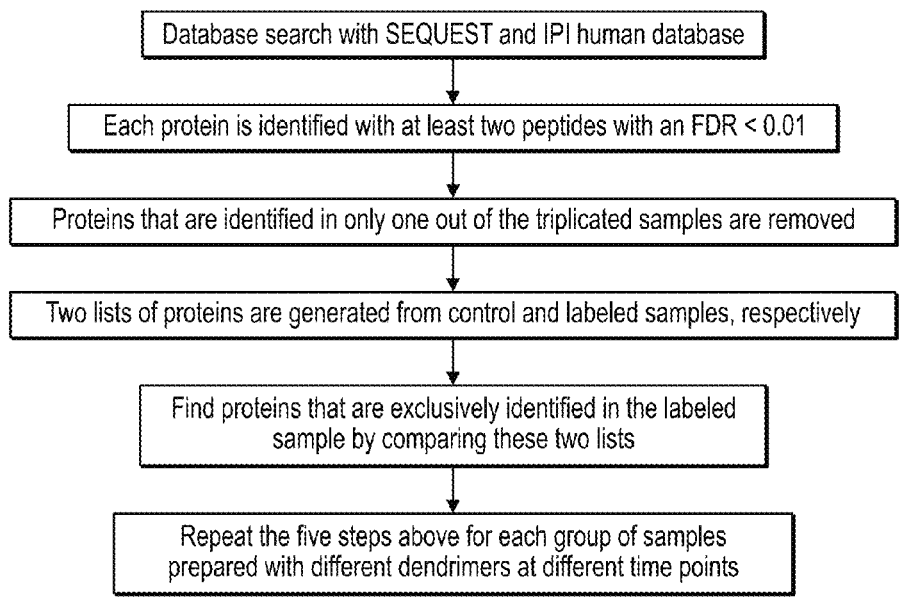
FIG. 8 is a flow chart illustrating a work flow for analysis of collected mass spectrometry data.

Then the labeled proteins were on-beads digested and subjected to LC-MS/MS analyses. The collected mass spectrometry data were searched against IPI human database using search engine SEQUEST, and the data analysis work flow is shown in FIG. 8.

The majority of non-specific binding proteins were removed using washing conditions, for example SDS or 8M urea, which are usually considered as eluting conditions in other experiments. Furthermore, in the data analysis process, highly strict criteria were employed to remove randomly identified proteins. First, proteins were identified with at least two peptides that have an FDR<0.01. Second, each protein had to be identified at least twice from the biological triplicate experiments. Third, proteins that appeared in both the labeled and control samples were considered as non-specific binding proteins and were removed. Only proteins exclusively identified in multiple labeled samples were considered as labeled proteins. With these strict criteria, 53 and 71 unique labeled proteins were identified exclusively from the in vivo delivery of the PEG handle dendrimer at 30 min and 6 hr, respectively. 37 proteins were identified from the MAP handle dendrimer delivered for 30 min and the samples of 6 hr delivery. These labeled proteins were involved in several cellular functional roles. A list of proteins identified after 30 min. from dendrimers with a PEG handle that are related to transportation or cellular responses is shown in Table 2. A list of proteins identified after 6 hr. from dendrimers with a PEG handle that are related to transportation or cellular responses is shown in Table 3. A list of proteins identified after 30 min. from dendrimers with a MAP handle that are related to transportation or cellular responses is shown in Table 4.

TABLE 2

| ID | Symbol | Entrez Gene Name | Location(s) | Type(s) | Functional Roles |
|---|---|---|---|---|---|
| IPI00217182.5 | DSP | desmoplakin | Plasma Membrane, cell-cell adherens junctions, desmosomes, intercellular junctions | other | Cell-cell contacts |
| IPI00789324.3 | JUP | junction plakoglobin | Plasma Membrane, cell-cell adherens junctions, cellular membrane, desmosomes, endoplasmic reticulum buds | other | Cell-cell contacts |
| IPI00790896.1 | GNB2 | guanine nucleotide binding protein (G protein), beta polypeptide 2 | Plasma Membrane | enzyme | Calcium channel regulator activity; G-protein coupled receptor binding |
| IPI00848226.1 | GNB2L1 | guanine nucleotide binding protein (G protein), beta polypeptide 2-like 1 | Cytoplasm | enzyme | Ion channel inhibitor activity |
| IPI00291916.6 | PHIP | pleckstrin homology domain interacting protein | Nucleus | other | Protein import into nucleus |
| IPI00940673.1 | TKT | transketolase | Cytoplasm, Endoplasmic reticulum membrane | enzyme | Metal ion and sugar binding |
| IPI00910830.1 | VDAC1 | voltage-dependent anion channel 1 | Cytoplasm, cell surface, cellular membrane, Endoplasmic Reticulum | ion channel | Protein, protein complex binding, voltage-dependent ionselective channel, transmembrane transport |

TABLE 3

| ID | Symbol | Entrez Gene Name | Location(s) | Type(s) | Functional Roles |
|---|---|---|---|---|---|
| IPI00455315.4 | ANXA2 | Annexin A2 | Plasma Membrane, cell junction, cell surface, early endosomes, late endosomes, exosomes | other | Body fluid secretion; cellular response to acid, positive regulation of vesicle fusion |
| IPI00025753.2 | DSG1 | desmoglein 1 | Plasma Membrane | other | cell borders, cell-cell contacts, cell periphery, cell surface, cellular membrane, desmosomes |
| IPI00013933.2 | DSP | desmoplakin | Plasma Membrane | other | Cell-cell contacts |

TABLE 3-continued

| ID | Symbol | Entrez Gene Name | Location(s) | Type(s) | Functional Roles |
|---|---|---|---|---|---|
| IPI00910221.2 | GNB2L1 | guanine nucleotide binding protein (G protein), beta polypeptide 2-like 1 | Cytoplasm | enzyme | Ion channel inhibitor activity |
| IPI00395772.5 | MYH9 | myosin, heavy chain 9, non-muscle | Cytoplasm | enzyme | Actin binding, Na+/K+-exchanging ATPase, cell-cell Contacts |
| IPI00007188.6 | SLC25A5 | solute carrier family 25 (mitochondrial carrier; adenine nucleotide translocator), member 5 | Cytoplasm, cellular membrane | transporter | Protein binding, transmembrane transport |

TABLE 4

| ID | Symbol | Entrez Gene Name | Location(s) | Type(s) | Functional Roles |
|---|---|---|---|---|---|
| IPI00935818.1 | AHCY | adenosyl-homocysteinase | Cytoplasm | enzyme | Chronic inflammatory response to antigenic stimulus |
| IPI00977640.1 | ATP1A1 | ATPase, Na+/K+ transporting, alpha 1 polypeptide | Plasma Membrane, endosomes, exosomes | transporter | Clathrin-coated vesicles, responsible for establishing and maintaining the electrochemical gradients of Na and K ions across the plasma membrane |
| IPI00790896.1 | GNB2 | guanine nucleotide binding protein (G protein), beta polypeptide 2 | Plasma Membrane | enzyme | Calcium channel regulator activity; G-protein coupled receptor binding |
| IPI00395772.5 | MYH9 | myosin, heavy chain 9, non-muscle | Cytoplasm, cell-cell adherens junctions, Exosomes | enzyme | Actin binding, Na+/K+-exchanging ATPase, cell-cell Contacts |
| IPI00293434.2 | SRP14 | signal recognition particle 14 kDa (homologous Alu RNA binding protein) | Cytoplasm | other | Cotranslational protein targeting to membrane, protein targeting to ER; response to drug |
| IPI00940673.1 | TKT | transketolase | Cytoplasm, Endoplasmic reticulum membrane | enzyme | Metal ion and sugar binding |

Figure 9:
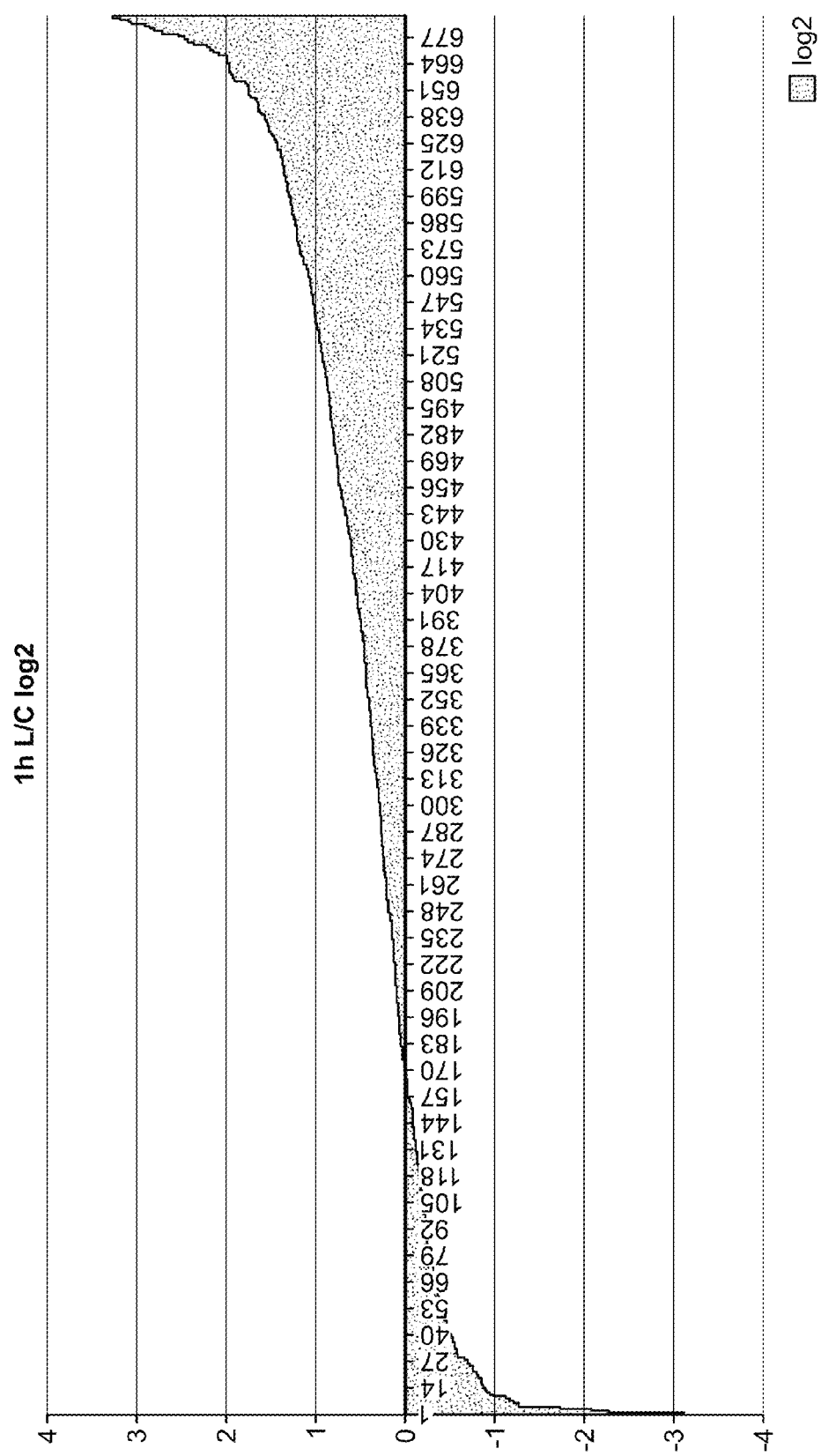
FIG. 9 is a graph showing that commonly identified proteins were more accumulated in the cross-linked samples.

Proteins in this list are surprisingly clustered into a few functional groups. Many of the proteins were repeatedly identified from varied samples, which are highlighted with a bold font. Additionally, commonly identified proteins were more accumulated in the cross-linked samples (FIG. 9). Furthermore, many proteins are known to form complexes or belong to the same protein family, for example, membrane proteins DSP and JUP are known to interact through their N-termini.

These two proteins together with DSG1 all reside in the desmosomes, which are intercellular junctions that tightly link adjacent cells. These three proteins were repeatedly identified in all the three groups of delivery experiments. This result supports the previous imaging results of dendrimer binding to cell membrane. It is widely accepted that dendrimers, viruses and many other nanoparticles are internalized through endocytosis pathways, especially clathrin-induced endocytosis. The mass spectrometry results here support these previous reports as well. Endosome proteins ANXA2 and ATP1A1 were identified in both the PEG- and MAP dendrimer delivery experiments. Specifically, ATP1A1 is known to exist in clathrin-coated vesicles. This protein is responsible for establishing and maintaining the electrochemical gradients of $Na^+$ and $K^+$ ions across the plasma. Another $Na^+/K^+$ exchanging ATPase protein MYH9 was also identified in both of the two dendrimer delivery experiments. MYH9 was previously reported to involve in virus transportations.

Dendrimers and viruses have similar sizes, and both of them are used to efficiently deliver drugs or genes into live cells. Thus, their delivery pathways may share similarities. It is also believed that other than endocytosis, viruses can penetrate cell membrane through other transporters or ion channels. Ion channel proteins GNB2 and GNB2N1 were repeatedly identified in the experiments, which indicate that dendrimers can be internalized through these pathways as well. Last but not the least, it is interesting to observe that the MAP-dendrimer 30 min delivery is more similar to that of the PEG-dendrimer 6 hour delivery. Proteins that reside on endoplasmic reticulum (ER) or target other proteins to ER start to appear. Several other proteins were identified as well, which are response to stimulations of antigen, acid or drugs. These results indicate that in the later stages of dendrimer delivery, cells begin to generate or locate specific proteins to respond to the dendrimer internalization.

Example 15

In Vivo Labeling at Different Time Points

Three time points ranging from 30 minutes after dendrimers were added into cell culture media to 2 hours were chosen as representative time points of different dendrimer delivery stages. Ultraviolet (UV) light irradiation resulted in cross-linking between dendrimers and proteins on their cellular entry and trafficking path. Proteins that interact with dendrimers in vivo were purified and quantified from three delivery time points. Dendrimers without the photo-reactive moiety was used as a negative control to avoid any chemical noise generated by exposing cells or cell lysates under ambient light.

Figure 10:
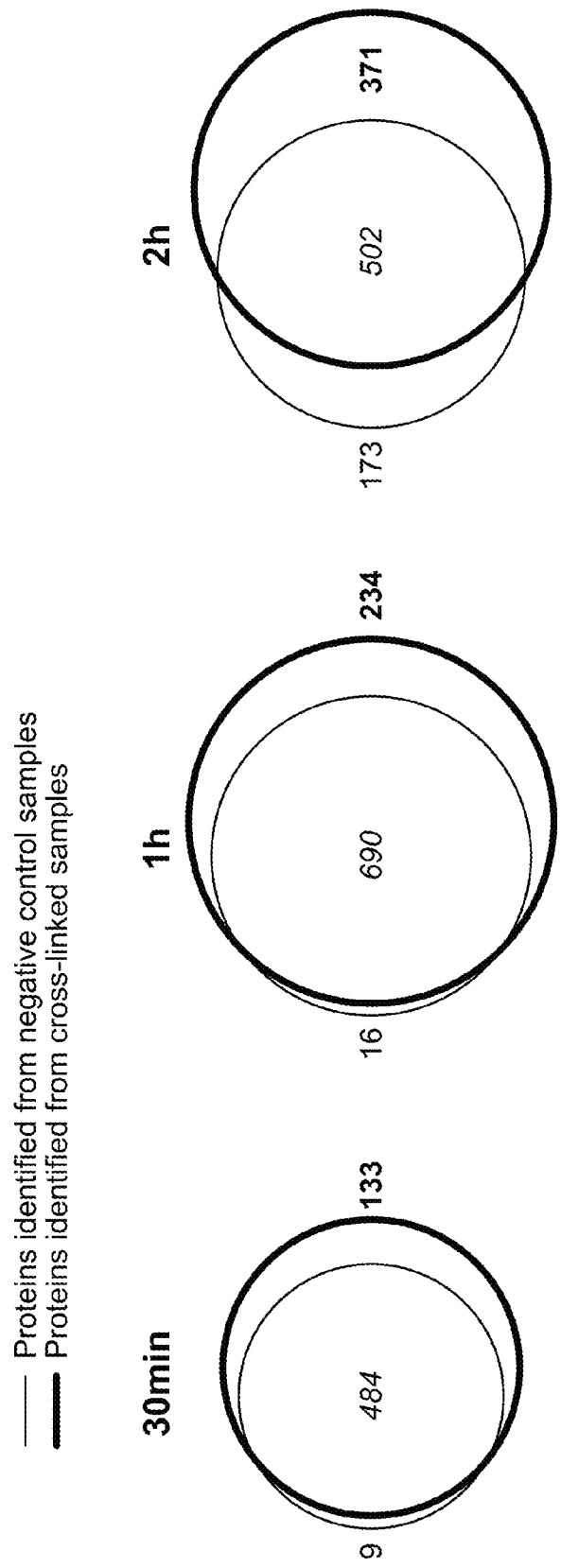
FIG. 10 is a Venn diagram of proteins identified from the negative control and cross-linked samples. Most of the proteins identified in the negative control samples are also included in the identification results from the cross-linked samples. Such result indicates the effective removing of non-specific binding proteins with the extremely harsh washing conditions.
Figure 11:
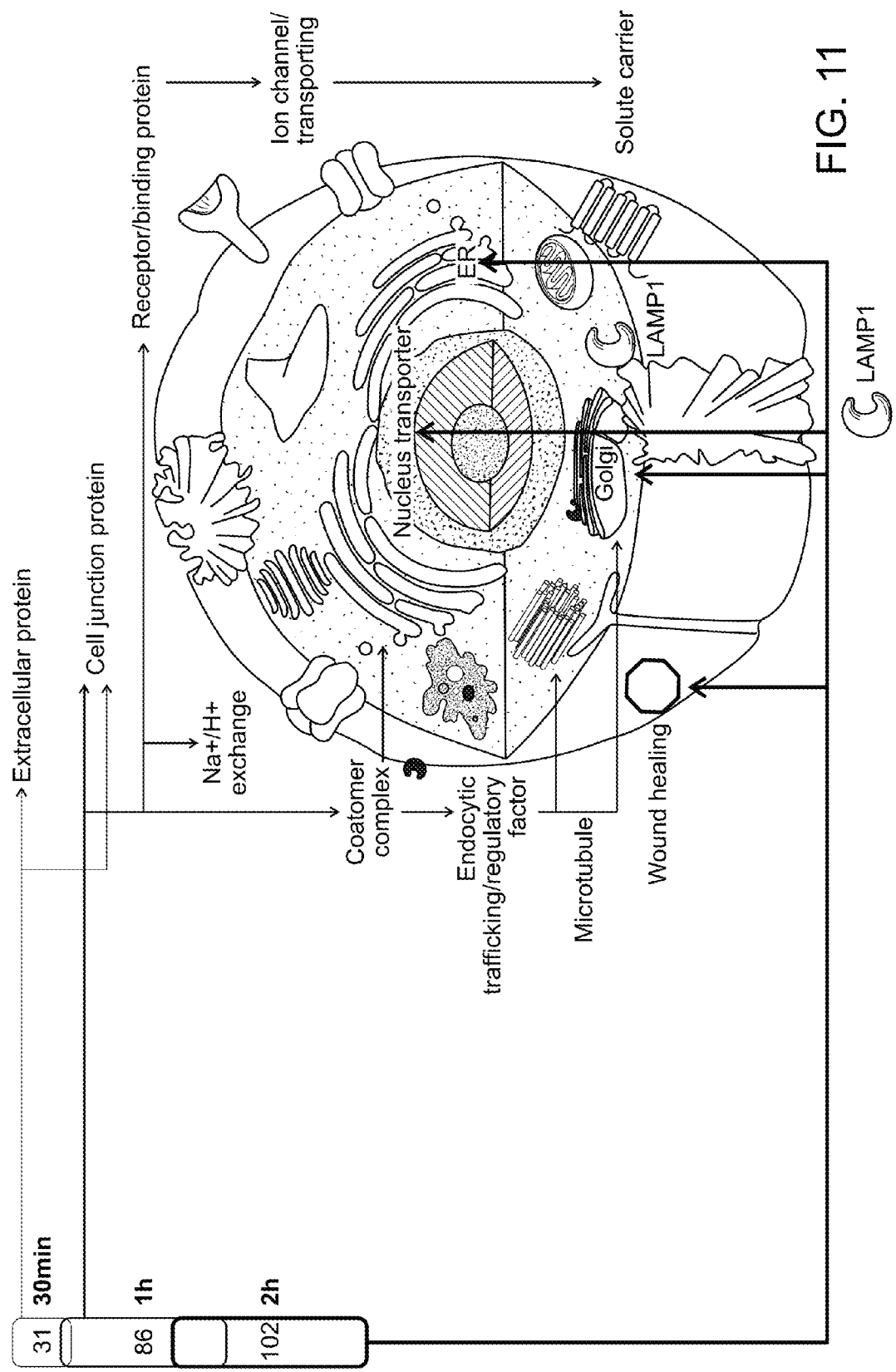
FIG. 11 is comparison of transportation related proteins identified at each time point. Delivery time related transportation proteins are pointed out with color coded arrows: 30 min green, 1 h, blue and 2 h red. Commonly identified transportation related proteins are not specified with arrows. Arrow thickness indicates protein numbers identified in each protein group. Thicker arrows indicate more proteins were identified at the specific time point.
Figure 12B:
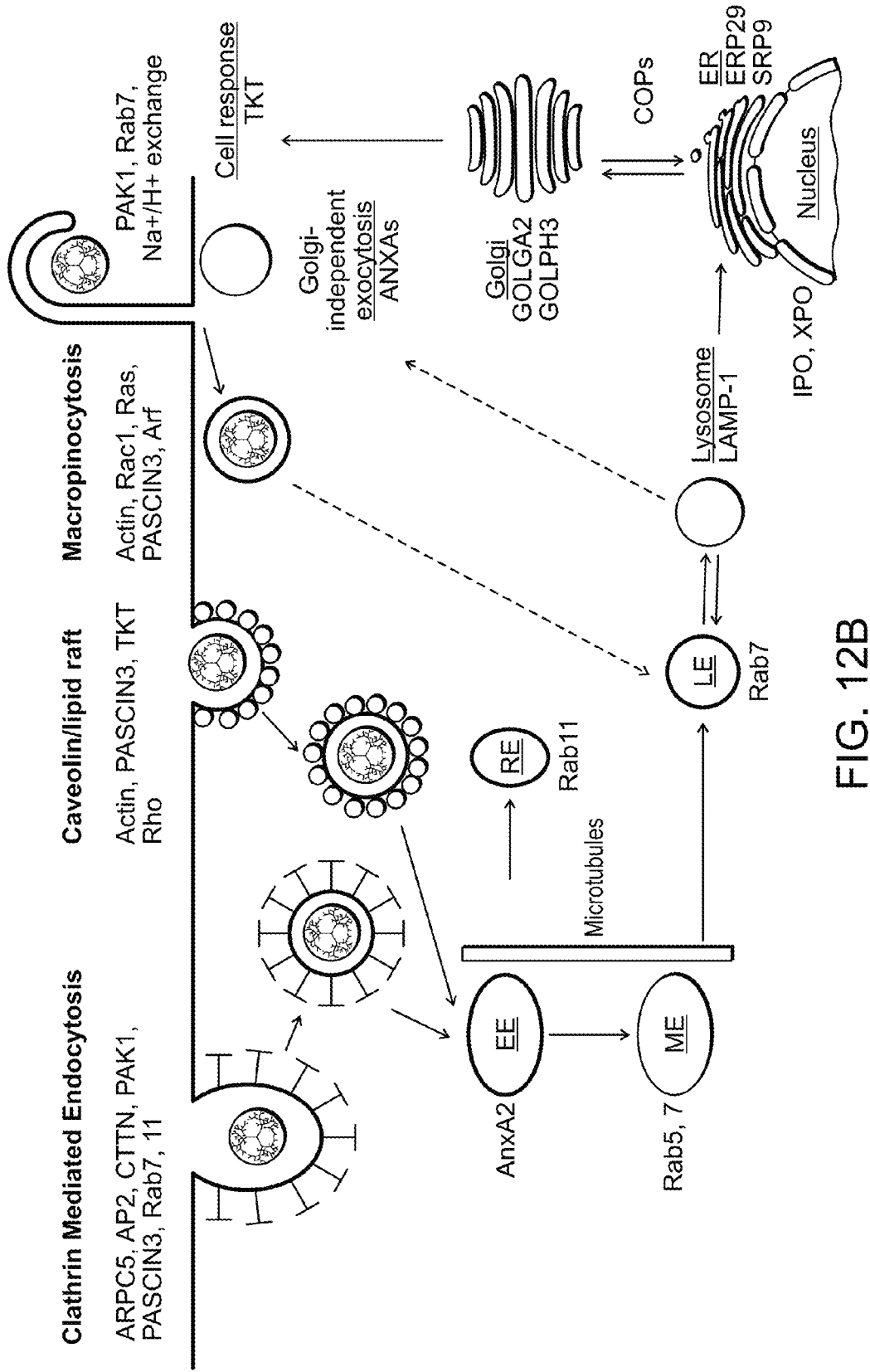

FIG. 10 summarizes the comparison between negative control samples and photo-cross-linked samples at three different time points: 30 minutes, 1 hour and 2 hours. In each group of experiments, most of the proteins identified in the negative control sample are also included in that of the cross-linked sample, which demonstrated the power of using extremely harsh washing conditions after affinity purification to remove non-specific binding proteins. At each time point, several hundreds of proteins were specifically identified from the cross-linked samples. Many of these proteins are involved in endocytic pathways, ion or molecule transportation, intra-cellular trafficking and cell responds processes. A comparison between the three time points is shown in FIG. 11. Many proteins that are localized in cell junction or extra-cellular space are identified in the 30-minute or 1 hour samples. Widely employed molecule transportation pathways, such as $Na^+/H^+$ exchange, ion channels and solute carrier proteins are identified from all the three time points. Endocytic characteristic proteins are identified from the later time points, 1- and 2-hour samples, while further intra-cellular trafficking, for example Golgi, Endoplasmic reticulum (ER) and nucleus transporter proteins were more identified at 2 hours. Especially, proteins involved in xenobiotics recognition and cell responses were found exclusively in the 2-hour sample, which clearly shows that the proteomics method is a powerful tool in identifying and differentiating cellular processes during cellular entrance and trafficking. It was found that proteins identified from the 30-minutes sample were involve more in cell junction, endocytic pathway proteins were observed in both 1- and 2-hour samples with similar amount, but the ER, Golgi and cell response proteins were more abundant in the later time point. From the proteomics results, several endocytic pathways were mapped in FIGS. 12A-B, including Clathrin-mediated, Macropinocytosis, Phagocytosis, Caveolin/lipid raft, IL2 and Arf6 pathways. Characteristic proteins involved in each pathway are shown in the figure. Many of these proteins (e.g. RAB, RAC, RAS and AP2 proteins) participate in multiple pathways. However CTTN and ARPC5 proteins are only shown as regulatory factors for the Clathrin-mediated endocytic pathway, therefore they are highlighted in the figure. Macropinocytosis is observed intensively likely due to the size of the engineered dendrimers. Macropinocytosis is more common for internalization of large molecules. Further dendrimer intra-cellular trafficking pathways were also mapped in this proteomics method. Proteins identified at different traveling stages are also shown in FIGS. 12A-B. The results demonstrated that the developed proteomics approach is un-biased, high throughput and can reveal molecular level information of cells under their native conditions.

Example 16

Additional and Alternative Embodiments

Figure 13:
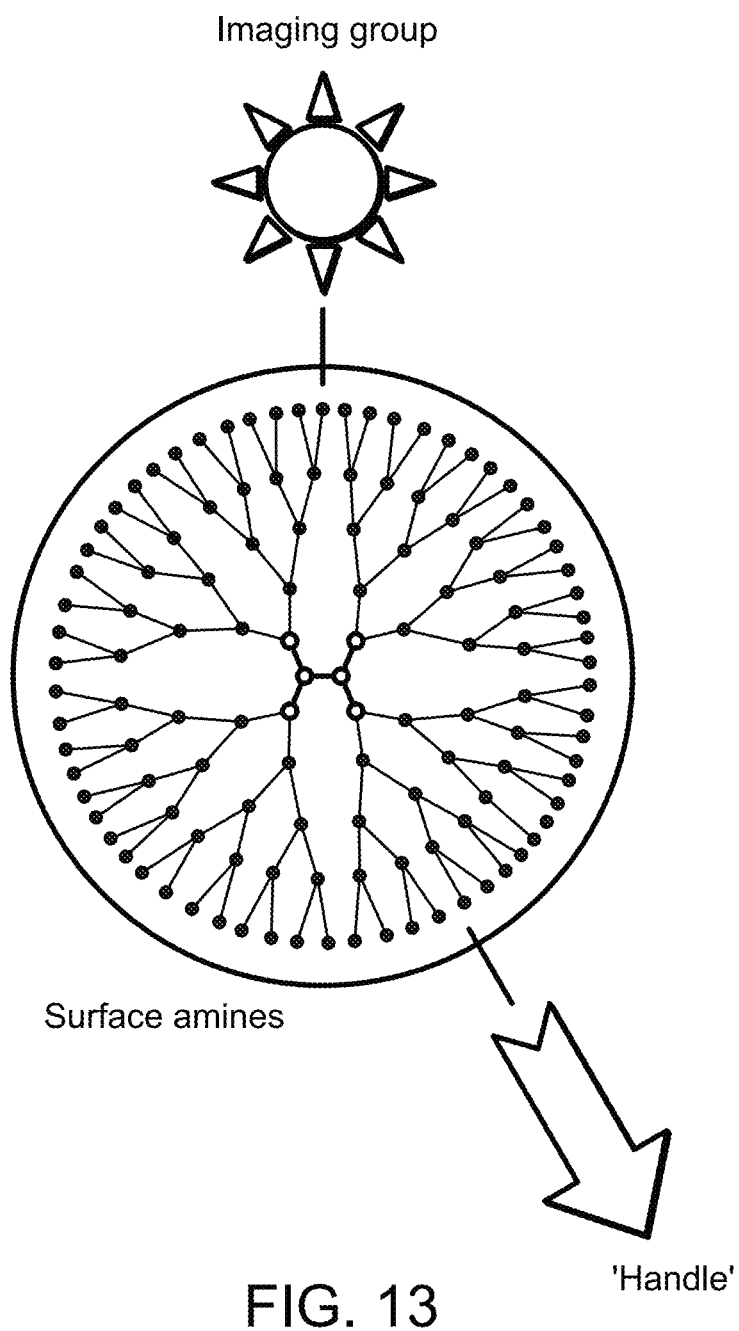
FIG. 13 is a diagram of a dendrimer in which the surface is coated with primary amines.
Figure 14:
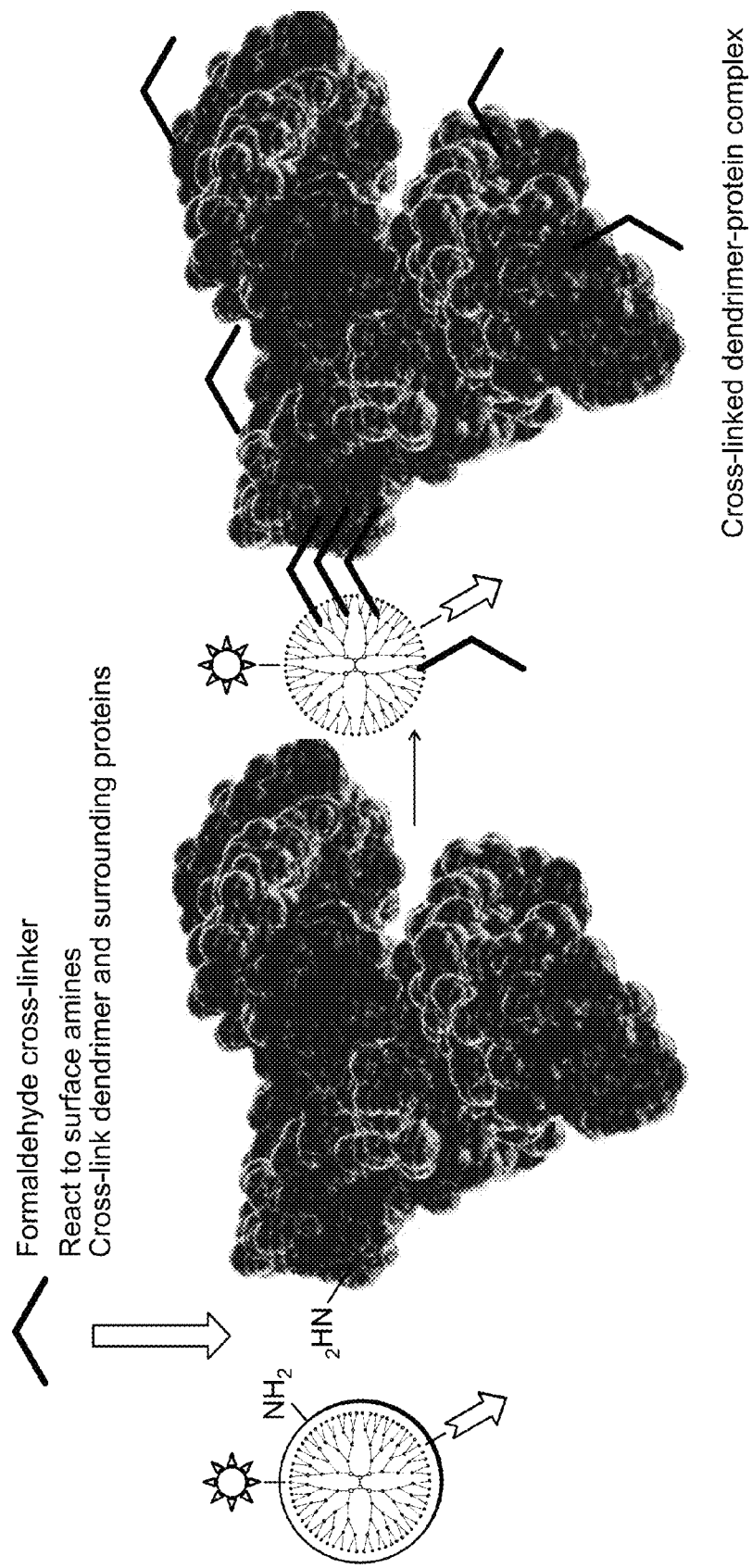
FIG. 14 is a diagram showing a reaction between a primary amine coated dendrimer and a cellular protein via formaldehyde as a cross-linking agent.

An alternative embodiment for the engineered dendrimers is shown in FIG. 13. In that embodiment, the surface of the dendrimer is coated with a primary amine, instead of a photoreactive functional group. To initiate the reaction in each preparation, a crosslinking agent, such as formaldehyde, disuccinimidyl suberate (DSS), or Dithiobis[succinimidyl propionate] (DSP) is introduced to the sample. FIG. 14 shows an example of the reaction when the formaldehyde is introduced. The advantages of using these commercially available cross-linkers include simpler synthesis of dendrimers and potentially higher cross-linking efficiency, because higher crosslinker concentrations can be used in the labeling reaction. The formaldehyde reacts universally with primary amines, so some specific is lost in this embodiment. However, the methods of the invention can be performed in this manner and still achieve acceptable results.

Figure 15:
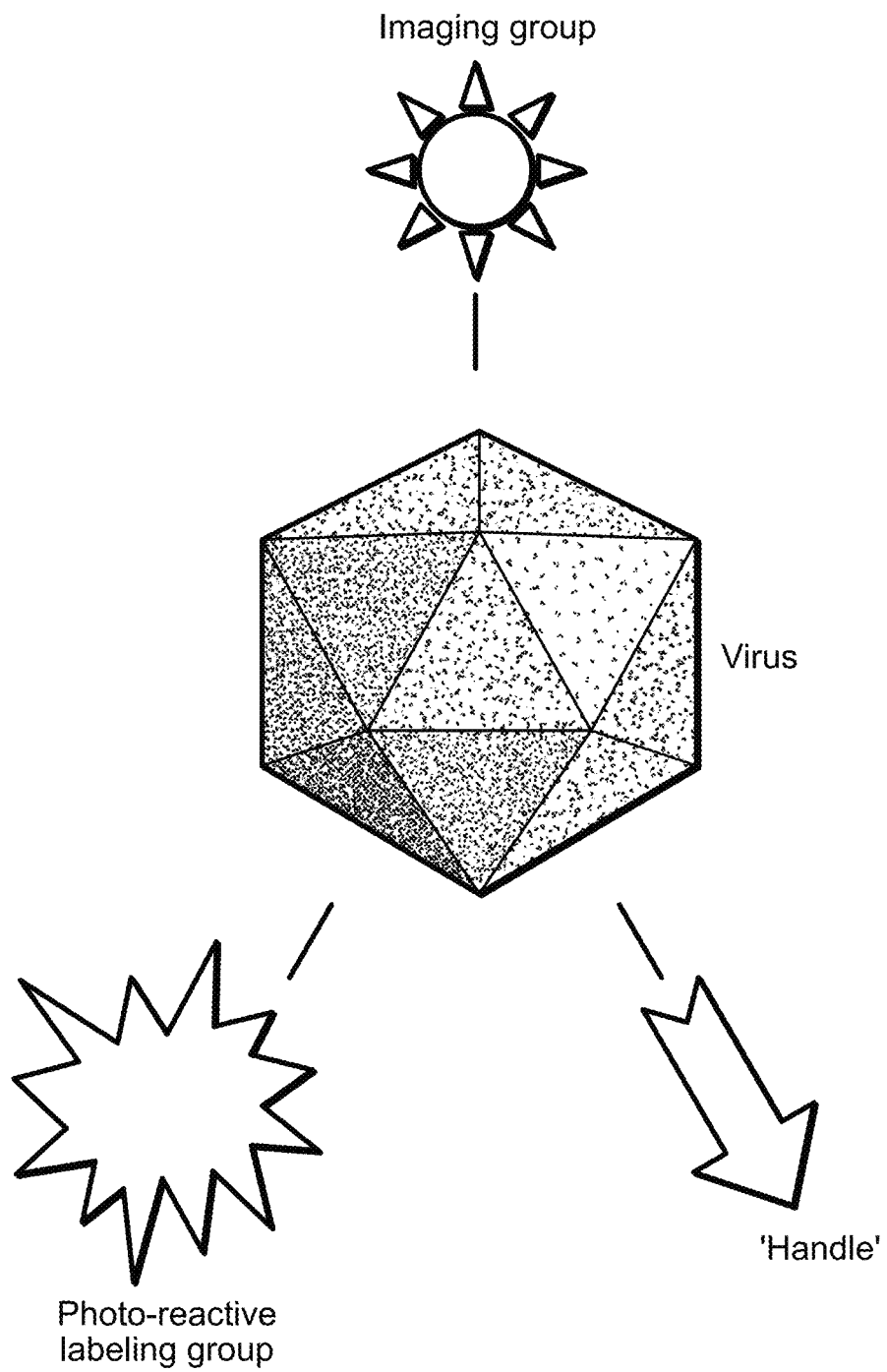
FIG. 15 is a diagraph shows an engineered virus.

FIG. 15 is an embodiment illustrating that the invention can also be extended to viruses. The embodiment in FIG. 15 shows how to engineer a capture unit with a virus as the member and then conduct pathway analyses using the engineered capture unit. Other biomedical delivery cargos can be

What is claimed is:

1. A method for isolating a plurality of proteins, the method comprising:
   preparing a plurality of sample preparations, each preparation comprising one or more intact cells;
   introducing a capture unit to a plurality of the preparations, the capture unit comprising a member that transiently interacts with one or more proteins in the cells and a reactive functional group;
   incubating the sample preparations;
   initiating a reaction at a different time points in a plurality of the preparations such that a protein within the cell that specifically interacts with the member of the capture unit becomes bound to the capture unit via the reactive functional group to form protein/capture unit complexes;
   lysing the cells according to the different time points at the initiating reaction step; and
   isolating the protein/capture unit complexes.

2. The method according to claim 1, wherein the member is capable of entering the cells through an entrance pathway of the cell.

3. The method according to claim 1, wherein reactive functional moiety does not interfere with the specific interaction between the member and the proteins within the cell.

4. The method according to claim 3, wherein the member is a nanoparticle.

5. The method according to claim 3, wherein the member is a microorganism.

6. The method according to claim 5, wherein the microorganism is a virus.

7. The method according to claim 1, wherein the member is a protein.

8. The method according to claim 1, wherein the reactive functional group comprises a photoreactive functional group.

9. The method according to claim 8, wherein light is used to initiate the reaction in each preparation.

10. The method according to claim 1, wherein the reactive functional group is a primary amine.

11. The method according to claim 10, wherein a chemical is used to initiate the reaction in each preparation.

12. The method according to claim 11, wherein the chemical is selected from the group consisting of formaldehyde, disuccinimidyl suberate (DSS), and Dithiobis[succinimidyl propionate] (DSP).

13. The method according to claim 1, wherein the capture unit further comprises a purification handle.

14. The method according to claim 13, wherein the capture units are separated from each sample preparation via the purification handle.

15. The method according to claim 1, further comprising analyzing the separated proteins.

16. The method according to claim 15, wherein the analyzing step uses a mass spectrometer.

17. The method according to claim 15, wherein analyzing is by liquid chromatography—mass spectrometry (LC-MS).

18. The method according to claim 15, wherein the capture unit further comprises a detectable label.

19. The method according to claim 18, wherein the label is an optically detectable label.

20. The method according to claim 1, wherein the reaction is initiated in a first sample preparation after 30 minutes of incubation, the reaction is initiated in a second sample preparation after 60 minutes of incubation, and the reaction is initiated in a third sample preparation after 120 minutes of incubation.

21. The method according to claim 1, wherein the member also transiently interacts with proteins outside of the cell.

22. The method according to claim 21, wherein the proteins are cell surface proteins.

* * * * *